(12) United States Patent
Bartizal et al.

(10) Patent No.: US 8,461,188 B2
(45) Date of Patent: Jun. 11, 2013

(54) THERAPEUTIC COMBINATION OF DAPTOMYCIN AND PROTEIN SYNTHESIS INHIBITOR ANTIBIOTIC, AND METHODS OF USE

(71) Applicant: Trius Therapeutics, Inc., San Diego, CA (US)

(72) Inventors: Kenneth F Bartizal, La Jolla, CA (US); Jeffrey B Locke, La Jolla, CA (US); Karen Joy Shaw, Poway, CA (US); Philippe G Prokocimer, Cardiff by the Sea, CA (US)

(73) Assignee: Trius Therapeutics, Inc., San Diego, CA (US)

( * ) Notice: Subject to any disclaimer, the term of this patent is extended or adjusted under 35 U.S.C. 154(b) by 0 days.

(21) Appl. No.: 13/655,704

(22) Filed: Oct. 19, 2012

(65) Prior Publication Data

US 2013/0102523 A1 Apr. 25, 2013

Related U.S. Application Data

(60) Provisional application No. 61/549,653, filed on Oct. 20, 2011.

(51) Int. Cl.
*A61K 31/4439* (2006.01)
*A61K 38/12* (2006.01)
*C07D 413/14* (2006.01)

(52) U.S. Cl.
USPC .......... 514/340; 546/271.4; 514/2.4; 514/2.7; 514/2.9; 514/21.1; 530/317

(58) Field of Classification Search
None
See application file for complete search history.

(56) References Cited

U.S. PATENT DOCUMENTS

| | | | |
|---|---|---|---|
| 6,468,967 B1 | 10/2002 | Oleson et al. | |
| 6,562,785 B1 | 5/2003 | Shapiro | |
| 6,794,490 B2 | 9/2004 | Hill et al. | |
| 6,852,689 B2 | 2/2005 | Oleson et al. | |
| RE39,071 E | 4/2006 | Baker et al. | |
| 7,262,268 B2 | 8/2007 | Morytko et al. | |
| 7,408,025 B2 | 8/2008 | Hill et al. | |
| 7,977,375 B2 | 7/2011 | Timmis et al. | |
| 2007/0155798 A1 | 7/2007 | Rhee et al. | |

FOREIGN PATENT DOCUMENTS

WO WO 00/18419 4/2000

OTHER PUBLICATIONS

Prockimer et al. ("Phase 2, Randomized, Double-Blind, Dose-Ranging Study Evaluating the Safety, Tolerability, Population Pharmacokinetics, and Efficacy of Oral Torezolid Phosphate in Patients with Complicated Skin and Skin Structure Infections," Antimicrobial Agents and Chemotherapy, (2011) 55, 583-592, published online Nov. 29, 2010).*

Betriu et al. ("Comparative Activities of TR-700 (Torezolid) against Staphylococcal Blood Isolates Collected in Spain," Antimicrobial Agents and Chemotherapy, (2010), 54, 2212-2215).*

Prockimer et al. ("Efficacy and Safety of Torezolid Phosphate (TR-701) in a Dose-Ranging Phase 2 Randomized, Double-Blind Study in Patients with Severe Complicated Skin and Skin Structure Infections (cSSSI)." Posters of the 49th ICAAC (L1-335), Sep. 12-15, 2009).*

Steenbergen et al. ("Daptomycin: a lipopeptide antibiotic for the treatment of serious Gram-positive infections," Journal of Antimicrobial Chemotherapy (2005) 55, 283-288).*

Chan et al. ("Comparative Efficacy of TR-701 (Prodrug of Torezolid), Vancomycin (Vanco) and Daptomycin (Dapto) in a Rabbit Model of Methicillin-Resistant *Staphylococcus aureus* (MRSA) Endocarditis." Posters of the 49th ICAAC (B-050), Sep. 12-15, 2009).*

Levine ("Clinical experience with daptomycin: bacteraemia and endocarditis," Journal of Antimicrobial Chemotherapy (2008) 62, Suppl. 3, iii35-iii39).*

Shoemaker et al. "A review of daptomycin for injection (Cubicin) in the treatment of complicated skin and skin structure infections," Therapeutics and Clinical Risk Management 2006:2(2), 169-174.*

Canton et al. "A potential role for daptomycin in enterococcal infections: what is the evidence?" J Antimicrob Chemother 2010; 65: 1126-1136.*

Jones et al. "TR-700 in vitro activity against and resistance mutation frequencies among Gram-positive pathogens," Journal of Antimicrobial Chemotherapy (2009) 63, 716-720.*

Allen et al., In vitro activities of quinupristin-dalfopristin and cefepime, alone and in combination with various antimicrobials, against multidrug-resistant staphylococci and enterococci in an in vitro pharmacodynamic model. Antimicrob. Agents Chemother., 46(8):2606-2612 (2002).

Arias et al., Genetic basis for in vivo daptomycin resistance in enterococci. N. Engl. J. Med., 365(10):892-900 (2011).

Baltz, Daptomycin: mechanisms of action and resistance, and biosynthetic engineering. Curr. Opin. Chem. Biol., 13(2):144-151 (2009).

Bertsche et al. Correlation of daptomycin resistance in a clinical *Staphylococcus aureus* strain with increased cell wall teichoic acid production and D-alanylation. Antimicrob Agents Chemother. 55(8):3922-3928 (2011).

Berti et al., Altering the proclivity towards daptomycin resistance in methicillin-resistant *Staphylococcus aureus* using combinations with other antibiotics. Antimicrob. Agents Chemother., 56(10):5046-5053 (2012).

(Continued)

*Primary Examiner* — Christina Bradley

(74) *Attorney, Agent, or Firm* — Knobbe, Martens, Olson & Bear LLP

(57) ABSTRACT

A therapeutic combination comprises an antibacterially effective amount of daptomycin, and an amount of protein synthesis inhibitor antibiotic effective to prevent the development of daptomycin non-susceptibility in bacteria. Related combination therapies and methods are also included.

18 Claims, 2 Drawing Sheets

OTHER PUBLICATIONS

Blondeau et al., Mutant prevention concentrations of fluoroquinolones for clinical isolates of *Streptococcus pneumoniae*. Antimicrob. Agents Chemother., 45(2):433-438 (2001).

Cafiso et al. Modulating activity of vancomycin and daptomycin on the expression of autolysis cell-wall turnover and membrane charge genes in hVISA and VISA strains. PloS One. 2012;7(1):e29573.

Camargo et al., Serial daptomycin selection generates daptomycin-nonsusceptible *Staphylococcus aureus* strains with a heterogeneous vancomycin-intermediate phenotype. Antimicrob. Agents Chemother., 52(12):4289-4299 (2008).

Chiang & Climo, Efficacy of linezolid alone or in combination with vancomycin for treatment of experimental endocarditis due to methicillin-resistant *Staphylococcus aureus*. Antimicrob. Agents Chemother., 47(9):3002-3004 (2003).

Cirioni et al., Daptomycin and rifampin alone and in combination prevent vascular graft biofilm formation and emergence of antibiotic resistance in a subcutaneous rat pouch model of staphylococcal infection. Eur. J. Vasc. Endovasc. Surg., 40(6):817-822 (2010).

Credito & Lin, Appelbaum PC. Activity of daptomycin alone and in combination with rifampin and gentamicin against *Staphylococcus aureus* assessed by time-kill methodology. Antimicrob. Agents Chemother., 51(4):1504-1507(2007).

Cui et al., An RpoB mutate on confers dual heteroresistance to daptomycin and vancomycin in *Staphylococcus aureus*. Antimicrob. Agents Chemother., 54(12):5222-5233 (2010.

Cui et al., Correlation between Reduced Daptomycin Susceptibility and Vancomycin Resistance in Vancomycin-Intermediate *Staphylococcus aureus*. Antimicrob. Agents Chemother., 50(3):1079-1082 (2006).

Dhand et al., Use of antistaphylococcal beta-lactams to increase daptomycin activity in eradicating persistent bacteremia due to methicillin-resistant *Staphylococcus aureus*: role of enhanced daptomycin binding. Clin. Infect. Dis., 53(2):158-163 (2011).

Drlica & Zhao, Mutant selection window hypothesis updated. Clin. Infect. Dis., 44(5):681-688 (2007).

Drusano et al., Standiford HC. Pharmacodynamics of a fluoroquinolone antimicrobial agent in a neutropenic rat model of *Pseudomonas* sepsis. Antimicrob. Agents Chemother., 37(3):483-490 (1993).

Entenza et al., In vitro prevention of the emergence of daptomycin resistance in *Staphylococcus aureus* and enterococci following combination with amoxicillin/clavulanic acid or ampicillin. Int. J. Antimicrob. Agents, 35(5):451-456 (2010).

Farrell et al., Investigation of the potential for mutational resistance to XF-73, retapamulin, mupirocin, fusidic acid, daptomycin, and vancomycin in methicillin-resistant *Staphylococcus aureus* isolates during a 55-passage study. Antimicrob. Agents Chemother., 55(3):1177-1181 (2011).

FDA Briefing Document for Anti-Infective Drugs Advisory Committee Meeting. Cubicin—(daptomycin for injection) for the treatment of *Staphylococcus aureus* bacteremia, including those with known or suspected infective endocarditis. Mar. 6, 2006.

Firsov et al., Testing the mutant selection window hypothesis with *Staphylococcus aureus* exposed to daptomycin and vancomycin in an in vitro dynamic model. J. Antimicrob. Chemother., 58(6):1185-1192 (2006).

Firsov et al. In vitro pharmacodynamic evaluation of the mutant selection window hypothesis using four fluoroquinolones against *Staphylococcus aureus*. Antimicrob. Agents Chemother., 47(5):1604-1613 (2003).

Fowler et al., Daptomycin versus standard therapy for bacteremia and endocarditis caused by *Staphylococcus aureus*. N. Engl. J. Med., 355(7):653-665 (2006).

Friedman et al., Genetic changes that correlate with reduced susceptibility to daptomycin in *Staphylococcus aureus*. Antimicrob. Agents Chemother., 50(6):2137-2145 (2006).

Garrigos et al. Efficacy of usual and high doses of daptomycin in combination with rifampin versus alternative therapies in experimental foreign-body infection by methicillin-resistant *Staphylococcus aureus*. Antimicrob Agents Chemother., 54(12):5251-5256 (2010).

Grohs et al., In vitro bactericidal activities of linezolid in combination with vancomycin, gentamicin, ciprofloxacin, fusidic acid, and rifampin against *Staphylococcus aureus*. Antimicrob. Agents Chemother., 47(1):418-420 (2003).

Hachmann et al., Reduction in membrane phosphatidylglycerol content leads to daptomycin resistance in *Bacillus subtilis*. Antimicrob. Agents Chemother., 55(9):4326-4337 (2011).

Hayden et al., Development of Daptomycin resistance in vivo in methicillin-resistant *Staphylococcus aureus*. J. Clin. Microbiol., 43(10):5285-5287 (2005).

Hermsen et al., Mutant prevention concentrations of ABT-492, levofloxacin, moxifloxacin, and gatifloxacin against three common respiratory pathogens. Antimicrob. Agents Chemother., 49(4):1633-1635 (2005).

Huang et al., Comparative bactericidal activities of daptomycin, glycopeptides, linezolid and tigecycline against blood isolates of Gram-positive bacteria in Taiwan. Clin. Microbiol. Infect., 14(2):124-129 (2008).

Jacqueline et al. In vitro activity of linezolid alone and in combination with gentamicin, vancomycin or rifampicin against methicillin-resistant *Staphylococcus aureus* by time-kill curve methods. J. Antimicrob. Chemother., 51(4):857-864 (2003).

Jorgensen & Crawford, Assessment of two commercial susceptibility test methods for determination of daptomycin MICs. J. Clin. Microbiol., 44(6):2126-2129 (2006).

Julian et al., Characterization of a daptomycin-nonsusceptible vancomycin-intermediate *Staphylococcus aureus* strain in a patient with endocarditis. Antimicrob. Agents Chemother., 51(9):3445-3448 (2007).

Kaatz et al., Mechanisms of daptomycin resistance in *Staphylococcus aureus*. Int. J. Antimicrobial. Agents., 28(4):280-287 (2006).

Kelesidis et al., Combination therapy with daptomycin, linezolid, and rifampin as treatment option for MRSA meningitis and bacteremia. Diagn. Microbiol. Infect Dis., 71(3):286-290 (2011).

Kelesidis et al., De novo daptomycin-nonsusceptible enterococcal infections. Emerg. Infect Dis., 18(4):674-676 (2012).

Kelley et al., Antimicrobial peptide exposure and reduced susceptibility to daptomycin: insights into a complex genetic puzzle. J. Infect. Dis., 206(8):1153-1156 (2012).

Kleinschmidt et al., In vitro exposure of community-associated methicillin-resistant *Staphylococcus aureus* (MRSA) strains to vancomycin: does vancomycin resistance occur? Int. J. Antimicrob. Agents, 27(2):168-170 (2006).

LaPlante et al., Activities of clindamycin, daptomycin, doxycycline, linezolid, trimethoprim-sulfamethoxazole, and vancomycin against community-associated methicillin-resistant *Staphylococcus aureus* with inducible clindamycin resistance in murine thigh infection and in vitro pharmacodynamic models. Antimicrob. Agents Chemother., 52(6):2156-2162 (2008).

LaPlante & Rybak, Impact of high-inoculum *Staphylococcus aureus* on the d of nafcillin, vancomycin, linezolid, and gmycin, alone and in combination with gentamicin, in an in vitro pharmacodynamic model. Antimicrob. Agents Chemother., 48(12):4665-4672 (2004).

Lee et al., Development of daptomycin nonsusceptibility with heterogeneous vancomycin-intermediate resistance and oxacillin susceptibility in methicillin-resistant *Staphylococcus aureus* during high-dose daptomycin treatment. Antimicrob. Agents Chemother., 54(9):4038-4040 (2010).

Mehta et al. VraSR two-component regulatory system contributes to mprF-mediated decreased susceptibility to daptomycin in in vivo-selected clinical strains of methicillin-resistant *Staphylococcus aureus*. Antimicrob. Agents Chemother., 56(1):92-102 (2012).

Mehta et al. β-Lactams Increase the Antibacterial Activity of Daptomycin against Clinical Methicillin-Resistant *Staphylococcus aureus* Strains and Prevent Selection of Daptomycin-Resistant Derivatives. Antimicrob. Agents Chemother., 56(12):6192-6200 (2012).

Miro et al., Addition of gentamicin or rifampin does not enhance the effectiveness of daptomycin in treatment of experimental endocarditis due to methicillin-resistant *Staphylococcus aureus*. Antimicrob. Agents Chemother., 53(10):4172-4177 (2009).

Mishra et al. In vitro cross-resistance to daptomycin and host defense cationic antimicrobial peptides in clinical methicillin-resistant *Staphylococcus aureus* isolates. Antimicrob. Agents Chemother., 55(9):4012-4018 (2011).

Mishra et al., Differential Adaptations of Methicillin-Resistant *Staphylococcus aureus* to Serial In Vitro Passage in Daptomycin: Evolution of Daptomycin Resistance and Role of Membrane Carotenoid Content and Fluidity Int J Microbiol 2012.683450 (2012).

Mishra et al., Analysis of cell membrane characteristics of in vitro-selected daptomycin-resistant strains of methicillin-resistant *Staphylococcus aureus*. Antimicrob. Agents Chemother., 53(6):2312-2318 (2009).

Moise et al., Susceptibility relationship between vancomycin and daptomycin in *Staphylococcus aureus*: facts and assumptions. The Lancet., 9:617-624 (2009).

Montero et al., Mechanisms of resistance to daptomycin in *Enterococcus faecium*. Antimicrob. Agents Chemother., 52(3):1167-1170 (2008).

Murthy et al., Daptomycin non-susceptible meticillin-resistant *Staphylococcus aureus* USA 300 isolate. J. Med. Microbiol., 57(Pt 8):1036-1038 (2008).

Nadrah & Strle, Antibiotic Combinations with Daptomycin for Treatment of *Staphylococcus aureus* Infections. Chem. Res. Pract., 2011:619321 (2011).

Palmer et al., Genetic basis for daptomycin resistance in enterococci. Antimicrob. Agents Chemother., 55(7):3345-3356 (2011).

Pankey et al., In vitro synergy of daptomycin plus rifampin against *Enterococcus faecium* resistant to both linezolid and vancomycin. Antimicrob. Agents Chemother., 49(12):5166-5168 (2005).

Parra-Ruiz et al., Activity of linezolid and high-dose daptomycin, alone or in combination, in an in vitro model of *Staphylococcus aureus* biofilm. J. Antimicrob. Chemother., 67(11):2682-2685 (2012).

Patel et al., Mechanisms of in-vitro-selected daptomycin-non-susceptibility in *Staphylococcus aureus*. Int. J. Antimicrob. Agents., 38(5):442-446 (2011).

Peleg et al., Whole genome characterization of the mechanisms of daptomycin resistance in clinical and laboratory derived isolates of *Staphylococcus aureus*. 7(1):e28316 (2012).

Pillai et al., Daptomycin nonsusceptibility in *Staphylococcus aureus* with reduced vancomycin susceptibility is independent of alterations in MprF. Antimicrob. Agents Chemother., 51(6):2223-2225 (2007).

Poeppl et al. Daptomycin, fosfomycin, or both for treatment of methicillin-resistant *Staphylococcus aureus* osteomyelitis in an experimental rat model. Antimicrob. Agents Chemother., 55(11):4999-5003 (2011).

Quinn B, Hussain S, Malik M, Drlica K, Zhao X. Daptomycin inoculum effects and mutant prevention concentration with *Staphylococcus aureus*. J Antimicrob Chemother. Dec. 2007;60(6):1380-1383.

Rand & Houck, Synergy of daptomycin with oxacillin and other beta-lactams against methicillin-resistant *Staphylococcus aureus*. Antimicrob. Agents Chemother., 48(8):2871-2875 (2004).

Rose et al. Daptomycin activity against *Staphylococcus aureus* following vancomycin exposure in an in vitro pharmacodynamic model with simulated endocardial vegetations. Antimicrob. Agents Chemother., 52(3):831-836 (2008).

Rose et al., Vancomycin tolerance in methicillin-resistant *Staphylococcus aureus*: influence of vancomycin, daptomycin, and telavancin on differential resistance gene expression. Antimicrob. Agents Chemother., 56(8):4422-4427 (2012).

Rose et al., Addition of ceftaroline to daptomycin after emergence of daptomycin-nonsusceptible *Staphylococcus aureus* during therapy improves antibacterial activity. Antimicrob. Agents Chemother., 56(10):5296-5302 (2012).

Sakoulas et al., Induction of daptomycin heterogeneous susceptibility in *Staphylococcus aureus* by exposure to vancomycin. Antimicrob. Agents Chemother., 50(4):1581-1585 (2006).

Sakoulas et al., Ampicillin enhances daptomycin- and cationic host defense peptide-mediated killing of ampicillin- and vancomycin-resistant *Enterococcus faecium*. Antimicrob. Agents Chemother., 56(2):838-844 (2012).

Saleh-Mghir et al., Adjunctive rifampin is crucial to optimizing daptomycin efficacy against rabbit prosthetic joint infection due to methicillin-resistant *Staphylococcus aureus*. Antimicrob. Agents Chemother., 55(10):4589-4593 (2011).

Sass et al. Genome sequence of *Staphylococcus aureus* VC40, a vancomycin- and daptomycin-resistant strain, to study the genetics of development of resistance to currently applied last-resort antibiotics. J. Bacteriol., 194(8):2107-2108 (2012).

Silverman et al., Resistance studies with daptomycin. Antimicrob. Agents Chemother., 45(6):1799-1802 (2011).

Singh et al., In vitro 24-hour time-kill studies of vancomycin and linezolid in combination versus methicillin-resistant *Staphylococcus aureus*. Antimicrob Agents Chemother. 53(10):4495-4497 (2009).

Steed et al., Novel daptomycin combinations against daptomycin-nonsusceptible methicillin-resistant *Staphylococcus aureus* in an in vitro model of simulated endocardial vegetations. Antimicrob. Agents Chemother., 54(12):5187-5192 (2010.

Steenbergen et al., Effects of daptomycin in combination with other antimicrobial agents: a review of in vitro and animal model studies. J. Antimicrob. Agents, 64(6):1130-1138 (2006).

Tenover et al., Characterisation of a *Staphylococcus aureus* strain with progressive loss of susceptibility to vancomycin and daptomycin during therapy. Int. J. Antimicrob Chemother., 33(6):564-568 (2009).

Tran et al., Native valve endocarditis caused by *Corynebacterium striatum* with heterogeneous high-level daptomycin resistance: collateral damage from daptomycin therapy? Antimicrob. Agents Chemother., 56(6):3461-3464 (2012).

Tsuji & Rybak, Short-course gentamicin in combination with daptomycin or vancomycin against *Staphylococcus aureus* in an in vitro pharmacodynamic model with simulated endocardial vegetations. Antimicrob. Agents Chemother., 49(7):2735-2745 (2005).

Vignaroli et al., Striking "seesaw effect" between daptomycin nonsusceptibility and beta-lactam susceptibility in *Staphylococcus haemolyticus*. Antimicrob. Agents Chemother., 55(5):2495-2496 (2011); author reply 2296-2497 (2011).

Wootton et al., Comparative bactericidal activities of daptomycin and vancomycin against glycopeptide-intermediate *Staphylococcus aureus* (GISA) and heterogeneous GISA isolates. Antimicrob. Agents Chemother., 50(12):4195-4197 (2006).

Yang et al., Enhanced expression of dltABCD is associated with the development of daptomycin nonsusceptibility in a clinical endocarditis isolate of *Staphylococcus aureus*. J. Infect. Dis., 200(12):1916-1920 (2009).

Yang et al., Cell wall thickening is not a universal accompaniment of the daptomycin nonsusceptibility phenotype in *Staphylococcus aureus*: evidence for multiple resistance mechanisms. Antimicrob. Agents Chemother., 54(8):3079-3085 (2010).

Yang et al., Daptomycin-oxacillin combinations in treatment of experimental endocarditis caused by daptomycin-nonsusceptible strains of methicillin-resistant *Staphylococcus aureus* with evolving oxacillin susceptibility (the "seesaw effect"). Antimicrob. Agents Chemother., 54(8):3161-3169 (2010).

Yang et al. Regulation of mprF in daptomycin-nonsusceptible *Staphylococcus aureus* strains. Antimicrob. Agents Chemother., 53(6):2636-2637 (2009).

Cunha et al., Methicillin-resistant *Staphylococcus aureaus* (MRSA) mitral valve acute bacterial endocarditis (ABE) in a patient with Job's syndrome (hyperimmunoglobulin E syndrome) successfully treated with linezolid and high-dose daptomycin, Heart and Lung, 37(1): 72-75 (2008).

International Search Report and Written Opinion dated Feb. 13, 2013 for PCT Application PCT/US2012/061048 filed Oct. 19, 2012.

\* cited by examiner

THERAPEUTIC COMBINATION OF DAPTOMYCIN AND PROTEIN SYNTHESIS INHIBITOR ANTIBIOTIC, AND METHODS OF USE

CROSS-REFERENCE TO RELATED APPLICATIONS

The application claims priority to U.S. Provisional Application No. 61/549,653 filed Oct. 20, 2011, which is incorporated herein by reference in its entirety.

BACKGROUND OF THE INVENTION

1. Field of the Invention

The present disclosure pertains to a therapeutic combination including daptomycin and related methods in which the development of daptomycin non-susceptibility is prevented in bacteria.

2. Description of the Related Art

Bacterial infections and other unwanted bacterial growth pose a continuing problem because bacteria evolve resistance to drugs used to kill them or impede their growth. Development of bacterial resistance necessitates a constant pipeline of new drugs to which bacterial pathogens have not yet developed resistance.

Some bacteria have now evolved resistance to almost all clinically useful antibacterial drugs, leaving physicians with few therapeutic or prophylactic choices. One especially pernicious strain is methicillin-resistant *Staphylococcus aureus* (commonly abbreviated as "MRSA"), which exhibits resistance to β-lactam antibiotics and cephalosporins. MRSA poses a severe threat in hospitals and nursing homes because strains found in those locations are often susceptible only to ceftaroline, telavancin, vancomycin, daptomycin, and the oxazolidinone linezolid. However, continuous and long term use of these drugs by patients cause bacteria to develop resistance in the patient, and thus the antiobiotics develop a reduced ability to treat the infection effectively.

The diminishing number of options for treating MRSA infections makes it highly desirable to find ways of delaying or eliminating the development of resistance to the few remaining drugs that retain efficacy.

To overcome such issues in the art, aspects of the invention are directed to a therapeutic combination wherein a compound unexpectedly prevents or reduces the development of daptomycin non-susceptibility.

SUMMARY

Particularly advantageous combinations, unexpectedly prevent the development of daptomycin non-susceptibility. In one embodiment, a therapeutic combination comprises an antibacterially effective amount of daptomycin, and an amount of a compound of Formula (I), or a pharmaceutically acceptable salt thereof, effective to prevent the development of daptomycin non-susceptible bacterial strains Formula (I)

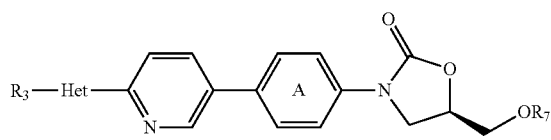

wherein: Het is tetrazolyl or oxadiazolyl; ring A is unsubstituted or has at least one fluorine substituent; $R_7$ is H, $PO(OH)_2$ or $PO(O)_2^{-2}(M^+)_2$, wherein M+ is a metal cation; $R_3$ is H or unsubstituted $C_{1-4}$ alkyl group. In some aspects, the therapeutic combination comprises

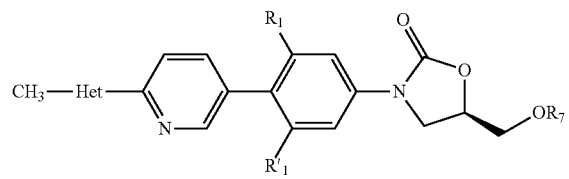

wherein at least one of $R_1$ and $R'_1$ is fluorine; and wherein the metal cation is Na+. For compounds in which only one of $R_1$ and $R'_1$ is fluorine, the other of $R_1$ and $R'_1$ is H. For example, the therapeutic combination may comprise

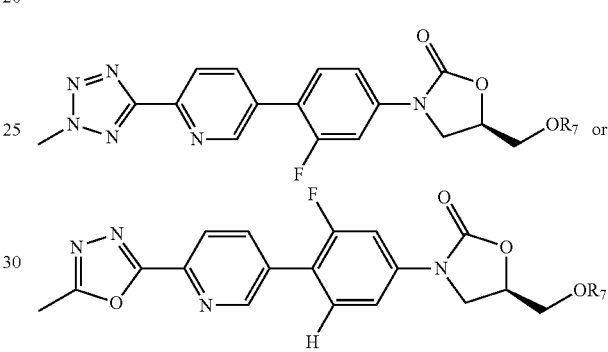

wherein the metal cation is $Na^+$.

In some aspects the compound of Formula (I) is

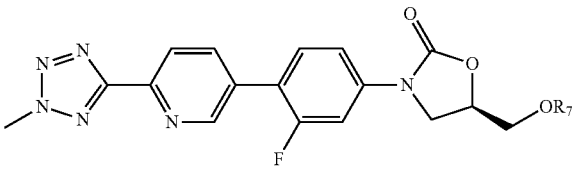

wherein the metal cation is $Na^+$.

The dosage of any of the above compounds included in Formula (I) may be, for example, no more than about 5 mg/kg, no more than about 4 mg/kg, no more than about 3 mg/kg, no more than about 2 mg/kg, no more than about 1 mg/kg, or no more than about 0.5 mg/kg. For instance, the unit dose of any of the above compounds included in Formula (I) may be 200 mg.

A therapeutic combination may comprise an antibacterially effective amount of daptomycin, and an amount of a protein synthesis inhibitor antibiotic, such as tedizolid, effective to prevent the development of daptomycin non-susceptibility. The amount of protein synthesis inhibitor antibiotic may be an amount less than the minimum inhibitory concentration (MIC) against a daptomycin-susceptible bacterium. Less than the MIC may be about one-half of the MIC or less, or about one-quarter of the MIC or less.

In some aspects, the combination of the daptomycin and the protein synthesis inhibitor antibiotic, such as tedizolid, may not synergistically enhance antibacterial potency, such as wherein the FICI is >0.50.

Some aspects of the combination do not include a membrane permeabilizing compound such as a cell wall synthesis inhibitor or an antibiotic such as cycloserine, vancomycin, bacitracin, β-lactams, cephalosporins, monobactams, and carbapenems. In some aspects, the combination does not include rifampicin or gentamicin.

The protein synthesis inhibitor antibiotic may be an oxazolidinone such as AZD5847, radezolid, PNU-100480, LCB01-0371, or tedizolid (formerly known as torezolid or TR-700).

The protein synthesis inhibitor may act through binding to a ribosome, a tRNA synthetase, a translation factor including but not limited to an elongation factor, an initiation factor or a termination factor.

In addition, the protein synthesis inhibitor antibiotic may be selected from the group of protein synthesis inhibitors consisting of aminoglycosides, tetracyclines, phenicols, pleuromutilins, macrolides, lincosamides, and streptogramins, such as retapamulin, tiamulin, lymecycline, mupirocin, chloramphenicol, florphenicol, tetracycline, netilmicin, streptomycin, kanamycin, clindamycin, lincomycin, and fusidic acid.

In one embodiment, a therapeutic combination comprises an antibacterially effective amount of daptomycin, and an amount of tedizolid effective to prevent the development of daptomycin non-susceptibility. For example, an amount of tedizolid may an amount less than the minimum inhibitory concentration (MIC) against a daptomycin-susceptible bacterium, such as a gram-positive bacterium. In some aspects, the daptomycin-susceptible bacterium is selected from the group consisting of *Staphylococcus, Streptococcus, Enterococcus, Clostridium, Corynebacterium*, and *Peptostreptococcus*. Further examples include *S. aureus, S. epidermidis, S. haemolyticus, S. hominis, S. saprophyticus, S. pneumoniae, S. pyogenes, S. agalactiae, S. avium, S. Bovis, S. lactis, S. sangius, E. faecalis, E. faecium, C. difficile, C. clostridiiforme, C. innocuum, C. perfringens, C. ramosum, L. monocytogenes, C. jeikeium, E. aerofaciens, E. lentum, L. acidophilus, L. casei, L. plantarum, P. anaerobius, P. asaccarolyticus, P. magnus, P. micros, P. prevotil, P. productus,* and *P. acnes*.

In some aspects, each component of the therapeutic combination, such as daptomycin and tedizolid, is formulated for separate or sequential administration; or the therapeutic combination is formulated for simultaneous administration.

Also contemplated are methods of treating a bacterial infection in a subject, comprising administering to the subject the therapeutic combination recited herein. For instance, a method of treating a bacterial infection in a subject may comprise selecting a bacterially infected subject; wherein a bacterium in the subject is susceptible to daptomycin; and administering a therapeutic combination comprising an antibacterially effective amount of a daptomycin, and an amount of a protein synthesis inhibitor antibiotic effective to prevent the development of daptomycin non-susceptibility; wherein, upon administration to the bacterially infected subject, the bacteria remain susceptible to daptomycin until the infection is resolved.

In some aspects, the bacterially infected subject has a bacterial infection that requires treatment for 5 days or greater, such as greater than two weeks. The bacterial infection may be caused by one or more bacterium described herein. The bacterial infection may be bacterial skin and skin structure infections, such as complicated skin and skin structure infections or acute bacterial skin and skin structure infections, or bacteremia. In some instances, the subject has endocarditis, also referred to as infective endocarditis (IE).

The method may include administering the therapeutic combination for at least two weeks.

In some aspects, the same amount of daptomycin is administered until the infection is resolved.

DETAILED DESCRIPTION OF THE PREFERRED EMBODIMENT

Figure 1:
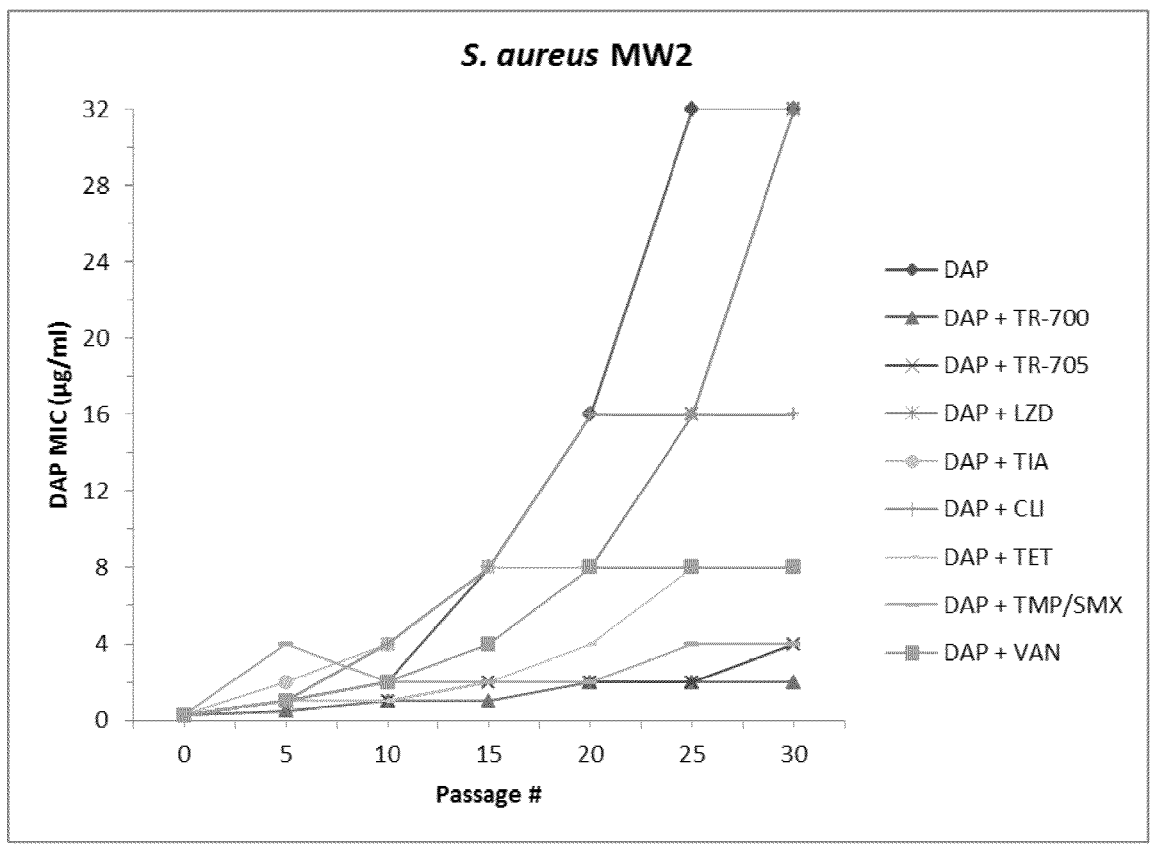
FIG. 1 shows the DAP MIC data only for *S. aureus* MW2.

U.S. RE39,071 (reissue of U.S. Pat. No. 5,912,226) is related to daptomycin (Cubist Pharmaceuticals). U.S. Pat. Nos. 6,852,689 and 6,468,967 (Cubist Pharmaceuticals) refer to methods for administering a therapeutically effective amount of daptomycin while minimizing skeletal muscle toxicity. The methods provide daptomycin administration and dosing interval of 24 hours or greater, which minimizes total muscle toxicity and allows for higher peak concentrations of daptomycin according to the patents, which is related to daptomycin's efficacy. The patent also relates to methods of administering lipopeptide antibiotics other than daptomycin while minimizing skeletal muscle toxicity by administering a therapeutically effective amount of the lipopeptide antibiotic the dosage interval that does not result in muscle toxicity. The patent states that "daptomycin would be expected to work synergistically with one or more co-administered antibiotics."

U.S. Pat. No. 7,262,268 (Cubist Pharmaceuticals) states that the administration methods include co-administration of antifungal or other antibacterial agents. Among the large group of antifungal and antibacterial agents that may be co-administered with the daptomycin stereoisomeric compounds or other lipopeptide antibiotics include aminoglycosides and oxazolidinones.

U.S. Pat. No. 6,562,785 refers to methods of killing bacteria, including antibiotic resistant bacteria, by contacting the bacteria with a membrane permeabilizing compound or combination of compounds and a membrane impermeant toxic agent for combination of agents, resulting in the death of the bacteria without substantial injury to the infected host or patient. According to the patent, the permeabilizing compound may be a cell wall synthesis inhibitor or an antibiotic such as cycloserine, vancomycin, bacitracin, β-lactams, cephalosporins, monobactams, and carbapenems. In one embodiment, the toxic agent is an inhibitor of nucleic acid synthesis, and inhibitor of protein synthesis, or an inhibitor of energy metabolism. In some aspects, the method of killing bacteria comprises contacting certain bacteria with a sublethal dose of an antibiotic in combination with a lethal amount of an agent, wherein said agent is impermeable to bacterial and eukaryotic cells with intact membranes in the absence of the antibiotic, resulting in the death of the bacteria.

Not all antibiotics can prevent the emergence of daptomycin-nonsusceptible bacteria. Gentamicin and rifampicin were unable to prevent the emergence of daptomycin resistance. Entenza, et al., International Journal of Antimicrobial Agents, 35 (2010) 451-56. For rifampicin, however, resistance was slightly delayed. The MIC of gentamicin and rifampicin increased two-fold and by a range of 2-32-fold, respectively in parallel to the increase in the daptomycin MIC. Amoxicillin/clavulanic acid or ampicillin prevented or greatly delayed selection of daptomycin-nonsusceptible mutants in *S. aureus* and enterococci respectively. Id.

Testing a combination of daptomycin with gentamicin or rifampicin has been reported. Nadrah et al., Chemotherapy Research and Practice, Volume 2011, Article ID 619321. Daptomycin-gentamicin combination for some strains showed synergy. Combinations of daptomycin and rifampicin were indifferent in assays. In an in vitro pharmacodynamic model of IE simulated endocardial vegetations and daptomycin-susceptible MRSA strain, addition of rifampicin and gentamicin substantially delayed or even antagonized a bactericidal effect of daptomycin.

Overall additive or indifferent effects of daptomycin combinations were observed; however, synergy was observed for certain isolates of vancomycin-resistant enterococci when exposed to daptomycin and rifampicin. Steenbergen et al., Journal of Antimicrobial Chemotherapy, 64, 1130-38 (2009). Unexpected synergy was demonstrated against methicillin-resistant Staphylococcus aureus by daptomycin and β-lactams. Id.

Daptomycin showed bactericidal synergy at 24 h when combined with oxacillin, imipenem and isepamicin. Huang et al., European Society of Clinical Microbiology and Infectious Disease, 14, 124-29 (2007).

Combination therapy with daptomycin and linezolid has been reported wherein the patient remained bacteremic despite combination therapy. Kelesidis, et al., Diagnosing Microbiology and Infectious Disease (except the Jul. 8, 2011). Here, bacteremia and CNS infection were successfully treated after combination treatment of daptomycin, and linezolid and rifampin (an RNA polymerase inhibitor, also known as rifampicin). Rifampin and daptomycin combinations were better than other combinations such as rifampin with vancomycin and linezolid. Garrigos, et al., Antimicrobial Agents and Chemotherapy, 54:12, 5251-56 (2010).

When linezolid was combined with vancomycin and ciprofloxacin, a slight antagonism was observed. Grohs et al, Antimicrobial Agents and Chemotherapy, 54:12, 418-20. See also, Chiang et al, Journal of Antimicrobial Chemotherapy, 47:9, 3002-04 (2003). Addition of linezolid resulted in a decrease of antibacterial activity for gentamicin and vancomycin, and linezolid was antagonistic to the early bactericidal activity for gentamicin. Linezolid, in combination with rifampicin showed an additive interaction for susceptible strains and inhibited rifampicin-resistant variants. Jacqueline et al., Journal of Antibacterial Chemotherapy, 51, 857-64 (2003).

Combination of daptomycin and fosphomysin was not advantageous. Poeppl et al., Antimicrob. Agents Chemother. Doi:10.112B/AAC.00584-11 (2011).

Against some strains tested, a combination of daptomycin and trimethoprim-sulfamethoxazole (TMP/SMX) provided the most consistent rapid bactericidal activity and superiority to daptomycin alone. The article states that "DAP plus LIN also showed superior activity to DAP alone against one of the tested strains, SA-684 . . . "; however, the curves shown in FIG. 1a for daptomycin alone versus a combination of daptomysin and linezolid do not significantly differ for most of the time frames. Steed et al., Antimicrobial Agents and Chemotherapy, 54:12, 5187-92 (2010).

In some aspects, the therapeutic combinations described herein do not include a membrane permeabilizing compound such as a cell wall synthesis inhibitor or an antibiotic such as cycloserine, vancomycin, bacitracin, β-lactams, cephalosporins, monobactams, and carbapenems. In some aspects, the therapeutic combinations do not include rifampicin or gentamicin.

Embodiments of the therapeutic combinations described herein are supported by the Example below and the Figures.

Figure 2:
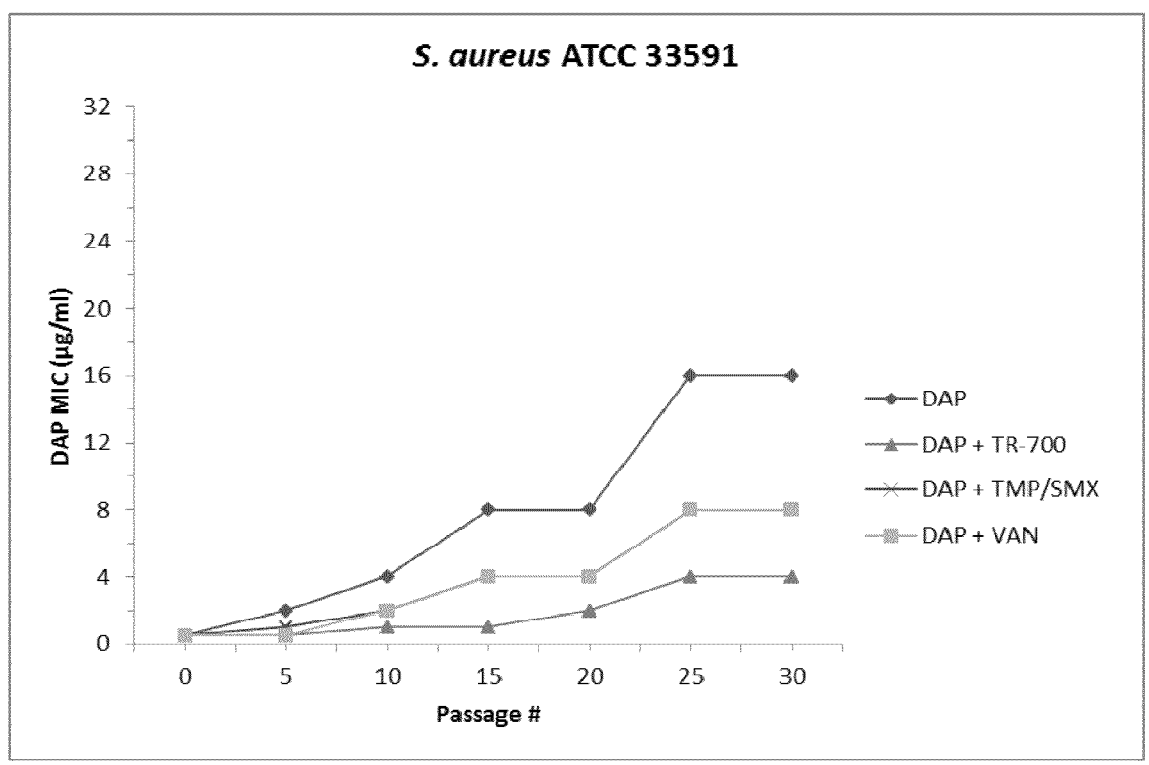
FIG. 2 shows the DAP MIC data only for *S. aureus* ATCC 33591.

Through use of a gradient plate serial passage methodology highly daptomycin nonsusceptible (DAP$^{ns}$) mutants in MRSA strain backgrounds MW2 and ATCC 33591 were generated (FIGS. 1, 2). Passaging of MW2 in the presence of DAP alone or in combination with sub-inhibitory concentrations (¼ MIC) of tedizolid (TR-700), TR-705 (oxadiazole analog of TR-700), linezolid (LZD), tiamulin (TIA), clindamycin (CLI), tetracycline (TET), trimethoprim/sulfamethoxazole (TMP/SMX) or vancomycin (VAN) resulted in the selection of DAP$^{ns}$ strains in all groups by the end of the experiment (i.e. DAP MIC values >1 μg/ml CLSI breakpoint). However, MIC values in the MW2 selection groups containing TR-700 (tedizolid) had the lowest fold shift increases in DAP MIC values after 30 passages (16-fold lower than DAP-only control) in the total population MIC values (Table 2). The TR-700 oxadiazole analog, TR-705, behaved similarly in the MW2 background (8-fold lower DAP MIC than the DAP-only control). The ability of TR-700 to prevent the emergence of DAP nonsusceptibility was also observed when a subset of the MW2 passage conditions was analyzed in S. aureus ATCC 33591 (TR-700 passage group DAP MIC of ≦1 μg/ml through P15 and 4-fold lower than DAP-only control) (Table 3). Consistent with its low S. aureus mutation frequency (Locke, J. B., et al., 2009. Antimicrob. Agents Chemother. 53:5265-5274), TR-700 co-selection groups did not demonstrate reduced susceptibility to TR-700 over the course of 30 passages. The ability of TR-700 and TR-705 to prevent the emergence of DAP$^{ns}$ is unexpected in light of the fact that the other oxazolidinone comparator compound, LZD, passage group showed no effect on preventing DAP$^{ns}$ in this study. These data are consistent however with a similar DAP combination passage study which found that co-selection with a subinhibitory concentration of LZD did not have any effect on preventing the emergence of DAP$^{ns}$ S. aureus (Berti, A., et al. 2012. Antimicrob. Agents Chemother. 56:5046-53). The S. aureus LZD mutation frequency is >10-fold higher than for TR-700 (Locke, J. B., et al., 2009. Antimicrob. Agents Chemother. 53:5265-5274) and MIC increases of the co-selecting agent could increase the rate of DAP$^{ns}$ development, however no increases in LZD MIC values over WT were observed the LZD co-selection group. Thus, it is unexpected that TR-701 and TR-705 would show a suppression of emergence of resistance.

Synergy

In some aspects herein, the combination of daptomycin and the protein synthesis inhibitor does not synergistically enhance antibacterial potency.

FICI values have been interpreted in a variety of ways. See, Eliopoulos G and R Moellering. 1991. Antimicrobial combinations. In *Antibiotics in Laboratory Medicine, Third Edition*, edited by V Lorian. Williams and Wilkins, Baltimore, Md., PP. 432-492. Most commonly, FICI values have been defined as follows: ≦0.50, synergism; >0.50-2, indifference; >2, antagonism. More recently, FICI values have been interpreted as follows. A "synergistic interaction" was evidenced by inhibition of organism growth by combinations that are at concentrations significantly below the MIC of either compound alone, resulting in a low FICI value (≦0.50). See, Odds F C. 2003. Synergy, antagonism, and what the chequerboard puts between them. J. Antimicrob. Chemother. 52(1):1. The interpretation of "no interaction" results in growth inhibition at concentrations below the MICs of the individual compounds, but the effect is not significantly different from the additive effects of the two compounds, resulting in an FICI value of >0.50 but less than or equal to 4.0. (The interpretation "no interaction" has previously been referred to as "additivity" or "indifference".) An "antagonistic interaction" results when the concentrations of the compounds in combination that are required to inhibit organism growth are greater than those for the compounds individually, resulting in an FIC value of >4.0. Thus, while the definition of synergism has remained constant, the definition of additivity/indifference has been broadened and re-named to "no interaction". In addition, the FICI value indicative of antagonism has been re-defined as >4. While there is no officially-sanctioned set of FICI criteria, the literature has been consistent in the use of ≦0.50 to define synergism.

Tedizolid and daptomycin show a lack of synergy as shown in Example 2.

Therapeutic Combinations

Daptomycin may be administered simultaneously with a protein synthesis inhibitor antibiotic. Alternatively, the protein synthesis inhibitor antibiotic may be successively administered after daptomycin is administered, or the daptomycin may be successively administered after the protein synthesis inhibitor antibiotic is administered. Furthermore, daptomycin may be separately administered some time after a protein synthesis inhibitor antibiotic administered, or a protein synthesis inhibitor antibiotic may be separately administered sometime after daptomycin is administered. The order and interval of administration can be appropriately selected by those skilled in the art.

Furthermore, the term "simultaneously" used herein refers to using the agents for treatment at about the same time. Those of skill in the art will recognize that the combination therapy in some cases can be administered simultaneously as a single composition or as distinct dosage forms administered at about the same time.

The term "separately" refers to using the agents for treatment separately at different times, for example, use daptomycin hours before or after the protein synthesis inhibitor antibiotic. The term "successively" refers to using the agents in order; for example, daptomycin is used first, and subsequently, after a set period of time, a protein synthesis inhibitor antibiotic is used. The combination therapy can be administered over a period that can be readily determined by the treating physician, but may often be within minutes or hours of each other, although in some circumstances longer intervals might be desirable.

Minimum Inhibitory Concentration (MIC) and Dosages

Determining the minimum inhibitory concentration (MIC) is well known in the art. Antibacterial efficacy of drugs is typically measured by determining in vitro the MIC of the drug for the individual bacterial species of interest. Thus, an antibacterially effective amount of daptomycin includes an amount that is above the MIC for the infection being treated. If more than one pathogen is present, the effective amount of daptomycin would be greater than or equal to the highest MIC of the infecting organisms. Generally, therapeutic regimens for bacterial infections are predicated upon administering one or more drug doses to the patient that achieve drug concentrations (m, for example, the blood) that at least meet and preferably exceed the MIC for at least a portion of the dosing interval. In some cases, the dosage may be maintained at the same level throughout the course of therapy or adjusted to increase or decrease the amount administered. In some aspects, the daptomycin dosage is not increased due to developing resistance (but may be increased for purposes of administering the appropriate dose during therapy).

Concentrations of the drug below the MIC do not, by definition inhibit the visible growth of a microorganism after overnight incubation lack therapeutic efficacy in the clinical context. Further, clinical practice strongly discourages exposure of bacterial pathogens to therapeutic regimens that lack efficacy because such regimens merely apply selection pressure to the pathogen, and thereby hasten development of resistance to the regimen. The efficacy of a regimen can be vitiated by, for example, administering sub-MIC doses of an antibacterial drug. For this reason, those of skill in the art generally do not intentionally administer a sub-MIC dose of an antibacterial drug.

The co-administration of daptomycin with a protein synthesis inhibitor antibiotic that inhibits protein synthesis, at a concentration/dosage of the latter that includes concentration/dosage that does not itself inhibit bacterial growth, impedes the development of bacterial resistance to daptomycin. The protein synthesis inhibitor may act through binding to a ribosome, a tRNA synthetase, a translation factor including but not limited to an elongation factor, an initiation factor or a termination factor. Suitable protein synthesis inhibitor antiobiotics include aminoglycosides, tetracyclines, phenicols, pleuromutilins, macrolides, lincosamides, and streptogramins. Additional protein synthesis inhibitor antiobiotics include retapamulin, tiamulin, lymecycline, mupirocin, chloramphenicol, florphenicol, tetracycline, netilmicin, streptomycin, kanamycin, clindamycin, lincomycin, and fusidic acid. Protein synthesis inhibitor antiobiotics also include oxazolidinones such as AZD5847, radezolid, PNU-100480, LCB01-0371, linezolid and tedizolid.

Useful oxazolidinones in the therapeutic combination are described in US Patent Publication No. 20070155798, which is a US national phase application of WO05/058886, which are hereby incorporated by reference in their entirety, and particularly for the purpose of describing oxazolidinones.

Oxazolidinone corresponding to Formula 1 defined below.

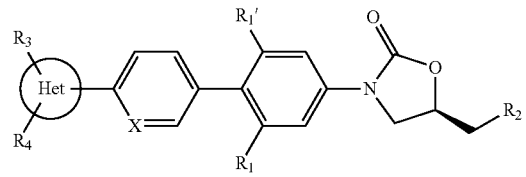

Formula 1

In the Formula 1, X represents carbon or nitrogen.

$R_1$ and $R_1'$ respectively represent hydrogen or fluorine.

$R_2$ represents —$NR_5R_6$, —$OR_7$, triazol, fluorine, alkylphosphate, monophosphate or a metal salt of phosphate;

$R_5$ and $R_6$, which are the same or different, respectively represent hydrogen, $C_{1-4}$ alkyl group or acetyl; and $R_7$ is hydrogen, $C_{1-3}$ alkyl group or acylated amino acid. When the $R_7$ is acylated amino acid, amino acid refers to alanine, glycine, proline, isoleucine, leucine, phenylalanine, β-alanine or valine.

Het, which is a heterocyclic ring or a hetero aromatic ring, refers to pyrrole, furan, piperazine, piperidine, imidazole, 1,2,4-triazol, 1,2,3-triazol, tetrazole, pyrazole, pyrrolidine, oxazole, isoxazole, oxadiazole, pyridin, pyrimidine, thiazole or pyrazine.

$R_3$ and $R_4$, which are the same or different, respectively refer to hydrogen, $C_{1-4}$ alkyl group that is substituted or unsubstituted with cyano, —$(CH_2)m$-$OR_7$ (m represents 0, 1, 2, 3, 4) or ketone. For example, $R_3$ may be methyl.

The derivatives of oxazolidinone corresponding to Formula 1 may be used in the form of a pharmaceutically acceptable salt, preferably an acid addition salt prepared by using pharmaceutically acceptable free acid. The free acid may be inorganic or organic. The inorganic free acid may comprise hydrochloric acid, bromic acid, sulfuric acid, phosphoric acid, etc. The organic free acid may include citric acid, acetic acid, lactic acid, maleic acid, fumaric acid, gluconic acid, methane sulfonic acid, glyconic acid, succinic acid, 4-toluenesulfonic acid, trifluoroacetic acid, galuturonic acid, embonic acid, glutamic acid, aspartic acid, etc.

Preferred compounds of the oxazolidinone derivatives according to the present invention include the following compounds (structures are described in Table 1):

1) (S)-3-(4-(2-(2-oxo-4-glycyloxymethylpylolidin-1-yl)pyridin-5-yl)-3-fluorophenyl)-2-oxo-5-oxazolidinylmethyl acetamide trifluoroacetic acid,
2) (S)-3-(4-(2-(4-glycyloxymethyl-1,2,3-triazol-1-yl)pyridin-5-yl)-3-fluorophenyl)-2-oxo-5-oxazolidinylmethyl acetamide trifluoroacetic acid,
3) (5)-3-(4-(2-(5-glycyloxymethylisoxazol-3-yl)pyridin-5-yl)-3-fluorophenyl)-2-oxo-5-oxazolidinylmethyl acetamide trifluoroacetic acid,
4) (R)-3-(4-(2-(2-methyltetrazol-5-yl)pyridin-5-yl)-3-fluorophenyl)-5-([1,2,4]triazol-1-yl)methyl oxazolidin-2-one,
5) (5)-3-(4-(2-(2-oxo-3-glycyloxypyrrolidine-1-yl)pyridin-5-yl)-3-fluorophenyl)-2-oxo-5-oxazolidinylmethyl acetamide trifluoroacetic acid,
6) (5)-3-(4-(2-(5-glycyloxymethyl-[1,2,4]oxadiazole-3-yl)pyridin-5-yl)-3-fluorophenyl)-2-oxo-5-oxazolidinylmethyl acetamide trifluoroacetic acid,
7) (5)-3-(4-(2-(5-glycyloxymethyl-4,5-dihydroisoxazole-3-yl)pyridin-5-yl)-3-fluorophenyl)-2-oxo-5-oxazolidinylmethyl acetamide trifluoroacetic acid,
8) (R)-3-(4-(2-(2-methyltetrazol-5-yl)pyridin-5-yl)-3-fluorophenyl)-5-([1,2,3]triazol-2-yl)methyl oxazolidin-2-one,
9) (R)-3-(4-(2-(2-methyltetrazol-5-yl)pyridin-5-yl)-3-fluorophenyl)-5-([1,2,3]triazol-1-yl)methyl oxazolidin-2-one,
10) (R)-3-(4-(2-(2-methyltetrazol-5-yl)pyridin-5-yl)-3-fluorophenyl)-5-hydroxymethyl oxazolidin-2-one,
11) (5)-3-(4-(4-(4,5-dimethyloxazol-2-yl)phenyl)-3-fluorophenyl)-2-oxo-5-oxazolidinylmethyl acetamide,
12) (R)-3-(4-(2-(2-methyltetrazol-5-yl)pyridin-5-yl)-3-fluorophenyl)-5-glycyloxymethyl oxazolidin-2-one trifluoroacetic acid,
13) (R)-3-(4-(2-(2-methyl-[1,3,4]oxadiazol-5-yl)pyridin-5-yl)-3-fluorophenyl)-5-([1,2,3]triazol-1-yl)methyl oxazolidin-2-one,
14) (R)-3-(4-(2-([1,2,4]triazol-1-yl)pyridin-5-yl)-3-fluorophenyl)-5-([1,2,3]triazol-1-yl)methyl oxazolidin-2-one,
15) (S)-3-(4-(2-(4,5-dimethyloxazol-2-yl)pyridin-5-yl)-3-fluorophenyl)-2-oxo-5-oxazolidinyl]methyl acetamide,
16) (R)-3-(4-(2-(2-methyl-[1,3,4]oxadiazol-5-yl)pyridin-5-yl)-3-fluorophenyl)-5-hydroxymethyl oxazolidin-2-one,
17) (R)-3-(4-(2-[1,2,4]triazol-1-yl pyridin-5-yl)-3-fluorophenyl)-5-hydroxymethyl oxazolidin-2-one,
18) (R)-3-(4-(2-(2-methyltetrazol-5-yl)pyridin-5-yl)-3-fluorophenyl)-5-fluoromethyl oxazolidin-2-one,
19) (S)-3-(4-(2-(imidazole-1-yl)pyridin-5-yl)-3-fluorophenyl)-5-aminomethyl oxazolidin-2-one hydrochloride,
20) (R)-3-(4-(2-(2-methyltetrazol-5-yl)pyridin-5-yl)-3-fluorophenyl)-5-(L-valyloxy)methyl oxazolidin-2-one trifluoroacetic acid,
21) (R)-3-(4-(4-(4,5-dimethyloxazol-2-yl)phenyl)-3-fluorophenyl)-5-hydroxymethyl oxazolidin-2-one,
22) (R)-3-(4-(2-([1,2,3]triazol-1-yl)pyridin-5-yl)-3-fluorophenyl)-5-glycyloxymethyl oxazolidin-2-one trifluoroacetic acid,
23) (R)-3-(4-(4-(4,5-dimethyloxazol-2-yl)phenyl)-3-fluorophenyl)-5-glycyloxymethyl oxazolidin-2-one trifluoroacetic acid,
24) (R)-3-(4-(2-([1,2,3]triazol-1-yl)pyridin-5-yl)-3-fluorophenyl)-5-hydroxymethyl oxazolidin-2-one,
25) (5)-3-(4-(2-([1,2,3]triazol-2-yl)pyridin-5-yl)-3-fluorophenyl)-2-oxo-5-oxazolidinylmethyl acetamide,
26) (5)-3-(4-(4-(4(S)-hydroxymethyl-4,5-dihydroxazole-2-yl)phenyl)-3-fluorophenyl)-2-oxo-5-oxazolidinylmethyl acetamide,
27) (R)-3-(4-(2-(2-methyl-[1,3,4]oxadiazole-5-yl)pyridin-5-yl)-3-fluorophenyl)-5-glycyloxymethyl oxazolidin-2-one trifluoroacetic acid,
28) (5)-3-(4-(4-(4-hydroxymethylthiazol-2-yl)phenyl)-3-fluorophenyl)-2-oxo-5-oxazolidinylmethyl acetamide,
29) (R)-3-(4-(2-([1,2,3]triazol-2-yl)pyridin-5-yl)-3-fluorophenyl)-5-hydroxymethyl oxazolidin-2-one,
30) (5)-3-(4-(4-(4-glycyloxymethylthiazol-2-yl)phenyl)-3-fluorophenyl)-2-oxo-5-oxazolidinylmethyl acetamide trifluoroacetic acid,
31) (S)-3-(4-(4-(4-cyanomethyl thiazol-2-yl)phenyl)-3-fluorophenyl)-2-oxo-5-oxazolidinylmethyl acetamide,
32) (R)-3-(4-(4-(4-cyanomethyl thiazol-2-yl)phenyl)-3-fluorophenyl)-5-hydroxymethyl oxazolidin-2-one,
33) (R)-3-(4-(2-(2-methyltetrazol-5-yl)pyridin-5-yl)-3-fluorophenyl)-5-methoxymethyl oxazolidin-2-one,
34) (R)-3-(4-(4-(4-cyanomethyl thiazol-2-yl)phenyl)-3-fluorophenyl)-5-glycyloxymethyl oxazolidin-2-one trifluoroacetic acid,
35) (R)-3-(4-(2-([1,2,3]triazol-2-yl)pyridin-5-yl)-3-fluorophenyl)-5-glycyloxymethyl oxazolidin-2-one trifluoroacetic acid,
36) (R)-3-(4-(4-(4-hydroxymethyl thiazol-2-yl)phenyl)-3-fluorophenyl)-5-([1,2,3]triazol-1-yl)methyl oxazolidin-2-one,
37) (R)-3-(4-(4-(4-glycyloxymethyl thiazol-2-yl)phenyl)-3-fluorophenyl)-5-([1,2,3]triazol-1-yl)methyl oxazolidin-2-one trifluoroacetic acid,
38) (R)-3-(4-(2-(2-methyltetrazol-5-yl)pyridin-5-yl)-3,5-difluorophenyl)-5-hydroxymethyl oxazolidin-2-one,
39) (R)-3-(4-(2-(2-methyl-[1,3,4]oxadiazol-5-yl)pyridin-5-yl)-3,5-difluorophenyl)-5-hydroxymethyl oxazolidin-2-one,
40) (R)-3-(4-(2-(2-methyltetrazol-5-yl)pyridin-5-yl)-3-fluorophenyl)-5-(N,N-dimethylaminomethyl)oxazolidin-2-one,
41) (R)-3-(4-(2-(2-methyltetrazol-5-yl)pyridin-5-yl)-3-fluorophenyl)-5-(N-methylaminomethyl)oxazolidin-2-one,
42) (R)-3-(4-(2-(2-methyltetrazol-5-yl)pyridin-5-yl)-3-fluorophenyl)-5-(L-alanyloxy)methyl oxazolidin-2-one trifluoroacetic acid,
43) (R)-3-(4-(2-(2-methyltetrazol-5-yl)pyridin-5-yl)-3-fluorophenyl)-5-(L-valyloxy)methyl oxazolidin-2-one hydrochloride,
44) (R)-3-(4-(2-(2-methyltetrazol-5-yl)pyridin-5-yl)-3-fluorophenyl)-5-(L-alanyloxy)methyl oxazolidin-2-one hydrochloride,
45) (R)-3-(4-(2-(2-methyltetrazol-5-yl)pyridin-5-yl)-3-fluorophenyl)-5-glycyloxymethyl oxazolidin-2-one hydrochloride,
46) (R)-3-(4-(2-(2-methyltetrazol-5-yl)pyridin-5-yl)-3-fluorophenyl)-5-(L-prolinyloxy)methyl oxazolidin-2-one trifluoroacetic acid,
47) (R)-3-(4-(2-(2-methyltetrazol-5-yl)pyridin-5-yl)-3-fluorophenyl)-5-(L-prolinyloxy)methyl oxazolidin-2-one hydrochloride,
48) (R)-3-(4-(2-(2-methyl-[1,3,4]oxadiazol-5-yl)pyridin-5-yl)-3-fluorophenyl)-5-glycyloxymethyl oxazolidin-2-one hydrochloride, 49) (R)-3-(4-(2-(2-methyltetrazol-5-yl)pyridin-5-yl)-3-fluorophenyl)-5-(β-alanyloxy)methyl oxazolidin-2-one trifluoroacetic acid,
50) (R)-3-(4-(2-(2-methyltetrazol-5-yl)pyridin-5-yl)-3-fluorophenyl)-5-(β-alanyloxy)methyl oxazolidin-2-one hydrochloride,
51) (R)-3-(4-(2-(2-methyl-[1,3,4]oxadiazol-5-yl)pyridin-5-yl)-3-fluorophenyl)-5-(L-alanyloxy)methyl oxazolidin-2-one trifluoroacetic acid,
52) (R)-3-(4-(2-(2-methyl-[1,3,4]oxadiazol-5-yl)pyridin-5-yl)-3-fluorophenyl)-5-(L-alanyloxy)methyl oxazolidin-2-one hydrochloride,
53) (R)-3-(4-(2-(2-methyl-[1,3,4]oxadiazol-5-yl)pyridin-5-yl)-3-fluorophenyl)-5-(L-valyloxy)methyl oxazolidin-2-one trifluoroacetic acid,
54) (R)-3-(4-(2-(2-methyl-[1,3,4]oxadiazol-5-yl)pyridin-5-yl)-3-fluorophenyl)-5-(L-valyloxy)methyl oxazolidin-2-one hydrochloride,
55) (R)-3-(4-(2-(2-methyl-[1,3,4]oxadiazol-5-yl)pyridin-5-yl)-3-fluorophenyl)-5-(L-prolinyloxy)methyl oxazolidin-2-one trifluoroacetic acid,
56) (R)-3-(4-(2-(2-methyl-[1,3,4]oxadiazol-5-yl)pyridin-5-yl)-3-fluorophenyl)-5-(L-prolinyloxy)methyl oxazolidin-2-one hydrochloride,
57) (R)-3-(4-(2-(2-methyl-[1,3,4]oxadiazol-5-yl)pyridin-5-yl)-3-fluorophenyl)-5-(β-alanyloxy)methyl oxazolidin-2-one trifluoroacetic acid,
58) (R)-3-(4-(2-(2-methyl-[1,3,4]oxadiazol-5-yl)pyridin-5-yl)-3-fluorophenyl)-5-(β-alanyloxy)methyl oxazolidin-2-one hydrochloride,
59) (R)-[3-(4-(2-(2-methyltetrazol-5-yl)pyridin-5-yl)-3-fluorophenyl)-2-oxo-5-oxazolidinyl]methyl disodiumphosphate,
60) (R)-[3-(4-(2-(2-methyl-[1,3,4]oxadiazol-5-yl)pyridin-5-yl)-3-fluorophenyl)-2-oxo-5-oxazolidinyl]methyl disodiumphosphate,
61) (R)-3-(4-(2-(1-methyltetrazol-5-yl)pyridin-5-yl)-3-fluorophenyl)-5-hydroxymethyl oxazolidin-2-one,
62) (R)-3-(4-(2-(1-methyltetrazol-5-yl)pyridin-5-yl)-3-fluorophenyl)-5-glycyloxymethyl oxazolidin-2-one trifluoroacetic acid,
63) (R)-3-(4-(2-(1-methyltetrazol-5-yl)pyridin-5-yl)-3-fluorophenyl)-5-glycyloxymethyl oxazolidin-2-one hydrochloride,
64) (R)-3-(4-(2-(1-methyltetrazol-5-yl)pyridin-5-yl)-3-fluorophenyl)-5-(L-alanyloxy)methyl oxazolidin-2-one trifluoroacetic acid,
65) (R)-3-(4-(2-(1-methyltetrazol-5-yl)pyridin-5-yl)-3-fluorophenyl)-5-(L-alanyloxy)methyl oxazolidin-2-one hydrochloride,
66) (R)-3-(4-(2-(1-methyltetrazol-5-yl)pyridin-5-yl)-3-fluorophenyl)-5-(L-valyloxy)methyl oxazolidin-2-one trifluoroacetic acid,
67) (R)-3-(4-(2-(1-methyltetrazol-5-yl)pyridin-5-yl)-3-fluorophenyl)-5-(L-valyloxy)methyl oxazolidin-2-one hydrochloride,
68) (R)-3-(4-(2-(1-methyltetrazol-5-yl)pyridin-5-yl)-3-fluorophenyl)-5-(β-alanyloxy)methyl oxazolidin-2-one trifluoroacetic acid,
69) (R)-3-(4-(2-(1-methyltetrazol-5-yl)pyridin-5-yl)-3-fluorophenyl)-5-(β-alanyloxy)methyl oxazolidin-2-one hydrochloride,
70) (R)-[3-(4-(2-(1-methyltetrazol-5-yl)pyridin-5-yl)-3-fluorophenyl)-2-oxo-5-oxazolidinyl]methyl disodiumphosphate,
71) (R)-3-(4-(2-(1-methyltetrazol-5-yl)pyridin-5-yl)-3-fluorophenyl)-5-([1,2,3]triazol-1-yl)methyl oxazolidin-2-one,
72) mono-[(R)-[3-(4-(2-(2-methyltetrazol-5-yl)pyridin-5-yl)-3-fluorophenyl)-2-oxo-5-oxazolidinyl]methyl]phosphate, and
73) mono-[(R)-[3-(4-(2-(1-methyltetrazol-5-yl)pyridin-5-yl)-3-fluorophenyl)-2-oxo-5-oxazolidinyl]methyl]phosphate.

TABLE 1

| Compound | Structure |
|---|---|
| 1 | 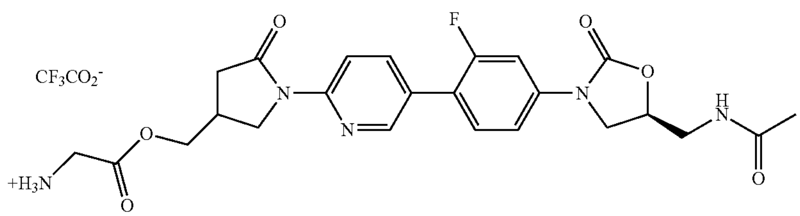 [SMILES: "CF3CO2-" ; CC(=O)NC[C@H]1CN(c2ccc(-c3ccc(N4CC(COC(=O)C[NH3+])CC4=O)nc3)c(F)c2)C(=O)O1] |
| 2 | 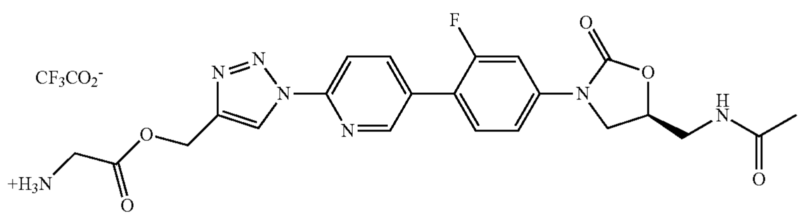 [SMILES: "CF3CO2-" ; CC(=O)NC[C@H]1CN(c2ccc(-c3ccc(-n4cc(COC(=O)C[NH3+])nn4)nc3)c(F)c2)C(=O)O1] |
| 3 | 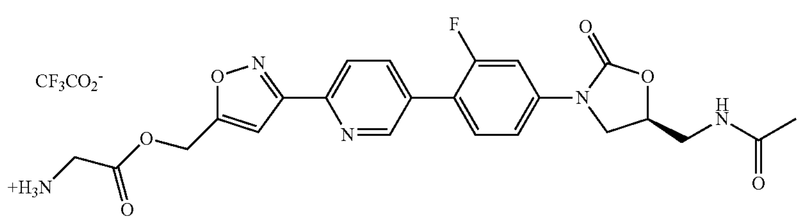 [SMILES: "CF3CO2-" ; CC(=O)NC[C@H]1CN(c2ccc(-c3ccc(-c4cc(COC(=O)C[NH3+])on4)nc3)c(F)c2)C(=O)O1] |

TABLE 1-continued

| Compound | Structure |
|---|---|
| 4 | 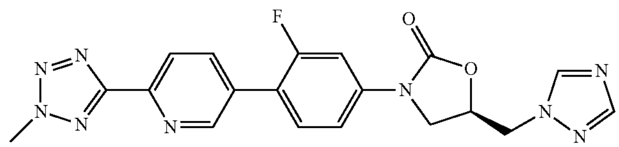 [SMILES: Cn1nnc(-c2ccc(-c3ccc(N4C[C@H](Cn5cncn5)OC4=O)cc3F)cn2)n1] |
| 5 | 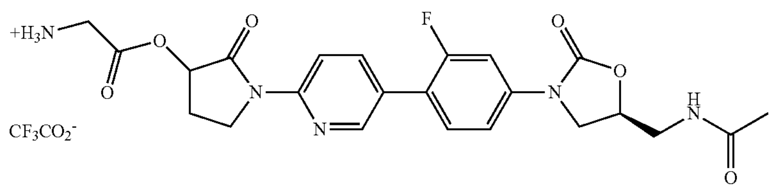 [SMILES: "CF3CO2-" ; CC(=O)NC[C@H]1CN(c2ccc(-c3ccc(N4CCC(OC(=O)C[NH3+])C4=O)nc3)c(F)c2)C(=O)O1] |
| 6 | 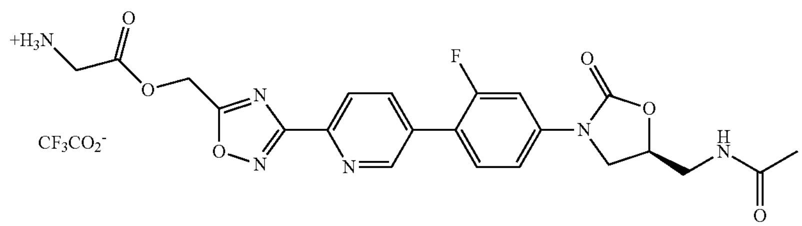 [SMILES: "CF3CO2-" ; CC(=O)NC[C@H]1CN(c2ccc(-c3ccc(-c4noc(COC(=O)C[NH3+])n4)nc3)c(F)c2)C(=O)O1] |
| 7 | 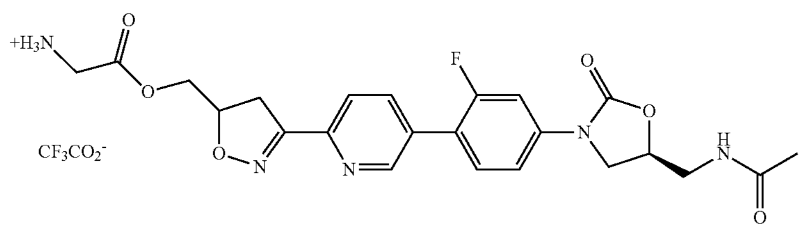 [SMILES: "CF3CO2-" ; CC(=O)NC[C@H]1CN(c2ccc(-c3ccc(C4=NOC(COC(=O)C[NH3+])C4)nc3)c(F)c2)C(=O)O1] |
| 8 | 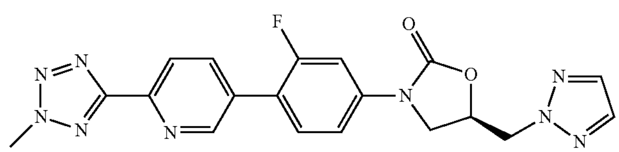 [SMILES: Cn1nnc(-c2ccc(-c3ccc(N4C[C@H](Cn5nccn5)OC4=O)cc3F)cn2)n1] |
| 9 | 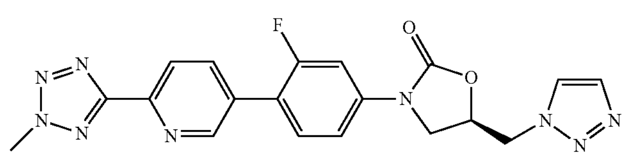 [SMILES: Cn1nnc(-c2ccc(-c3ccc(N4C[C@H](Cn5ccnn5)OC4=O)cc3F)cn2)n1] |
| 10 | 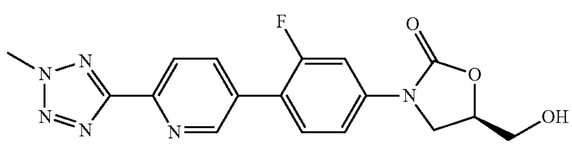 [SMILES: Cn1nnc(-c2ccc(-c3ccc(N4C[C@H](CO)OC4=O)cc3F)cn2)n1] |
| 11 | 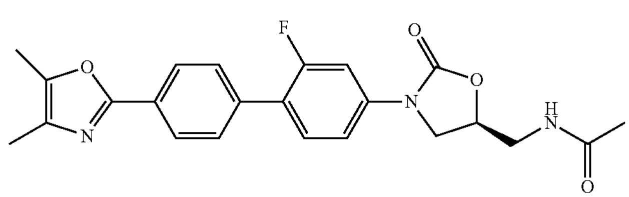 [SMILES: CC(=O)NC[C@H]1CN(c2ccc(-c3ccc(-c4nc(C)c(C)o4)cc3)c(F)c2)C(=O)O1] |

TABLE 1-continued

| Compound | Structure |
|---|---|
| 12 | (2-methyl-2H-tetrazol-5-yl)pyridine-fluorophenyl-oxazolidinone-CH2-O-C(O)-CH2-NH3+ CF3CO2- |
| 13 | (5-methyl-1,3,4-oxadiazol-2-yl)pyridine-fluorophenyl-oxazolidinone-CH2-(1H-1,2,3-triazol-1-yl) |
| 14 | (1H-1,2,4-triazol-1-yl)pyridine-fluorophenyl-oxazolidinone-CH2-(1H-1,2,3-triazol-1-yl) |
| 15 | (4,5-dimethyloxazol-2-yl)pyridine-fluorophenyl-oxazolidinone-CH2-NH-C(O)-CH3 |
| 16 | (5-methyl-1,3,4-oxadiazol-2-yl)pyridine-fluorophenyl-oxazolidinone-CH2-OH |
| 17 | (1H-1,2,4-triazol-1-yl)pyridine-fluorophenyl-oxazolidinone-CH2-OH |
| 18 | (2-methyl-2H-tetrazol-5-yl)pyridine-fluorophenyl-oxazolidinone-CH2-F |
| 19 | (1H-imidazol-1-yl)pyridine-fluorophenyl-oxazolidinone-CH2-NH2·HCl |
| 20 | (2-methyl-2H-tetrazol-5-yl)pyridine-fluorophenyl-oxazolidinone-CH2-O-C(O)-CH(NH3+)-CH(CH3)2 CF3CO2- |

TABLE 1-continued

| Compound | Structure |
|---|---|
| 21 | 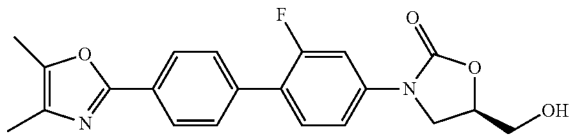 [SMILES: Cc1nc(-c2ccc(-c3ccc(N4C[C@H](CO)OC4=O)cc3F)cc2)oc1C] |
| 22 | 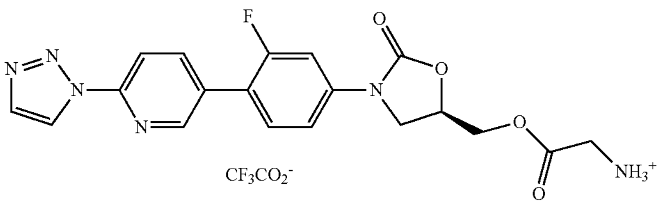 |
| 23 | 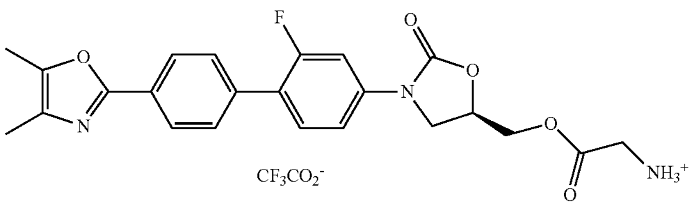 |
| 24 | 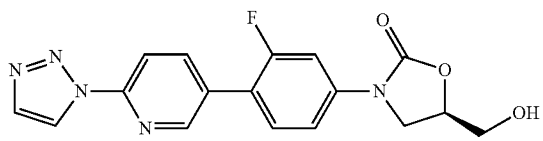 |
| 25 | 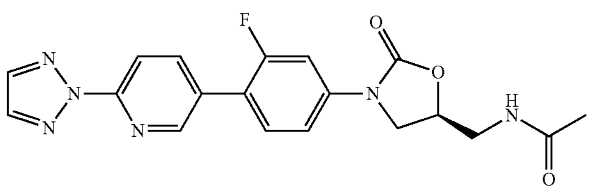 [SMILES: CC(=O)NC[C@H]1CN(c2ccc(-c3ccc(-n4nccn4)nc3)c(F)c2)C(=O)O1] |
| 26 | 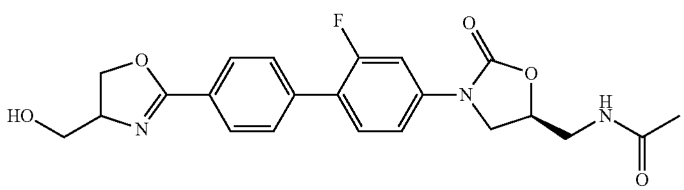 [SMILES: CC(=O)NC[C@H]1CN(c2ccc(-c3ccc(C4=NC(CO)CO4)cc3)c(F)c2)C(=O)O1] |
| 27 | 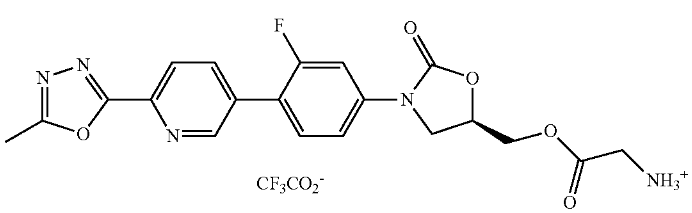 |
| 28 | 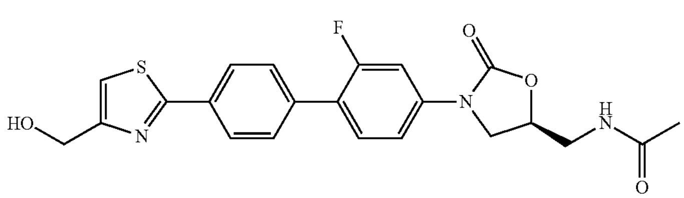 |

TABLE 1-continued

| Compound | Structure |
|---|---|
| 29 | 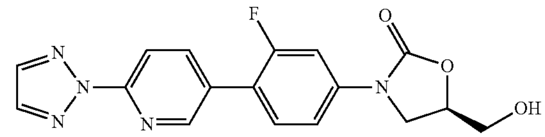 [SMILES: O=C1O[C@@H](CO)CN1c1ccc(-c2ccc(-n3nccn3)nc2)c(F)c1] |
| 30 | 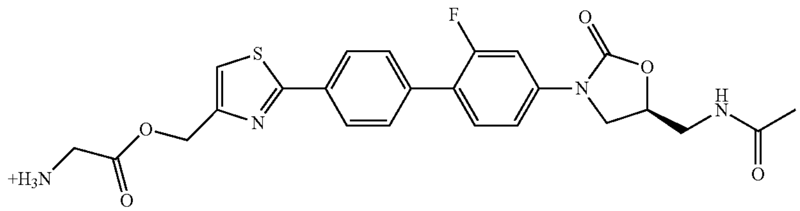 [SMILES: CC(=O)NC[C@H]1CN(c2ccc(-c3ccc(-c4nc(COC(=O)C[NH3+])cs4)cc3)c(F)c2)C(=O)O1] |
| 31 | 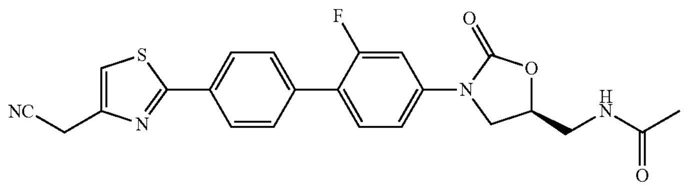 |
| 32 | 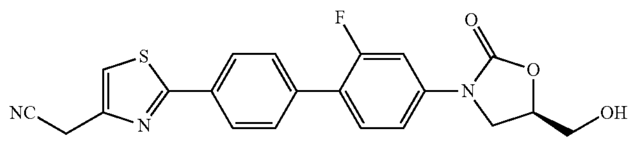 [SMILES: N#CCc1csc(-c2ccc(-c3ccc(N4C[C@H](CO)OC4=O)cc3F)cc2)n1] |
| 33 | 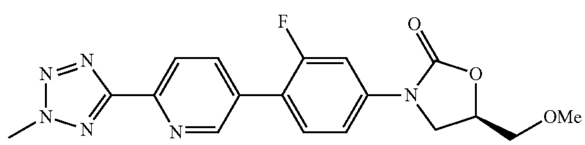 [SMILES: COC[C@H]1CN(c2ccc(-c3ccc(-c4nnn(C)n4)nc3)c(F)c2)C(=O)O1] |
| 34 | 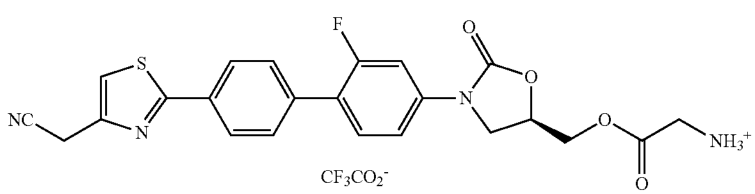 |
| 35 | 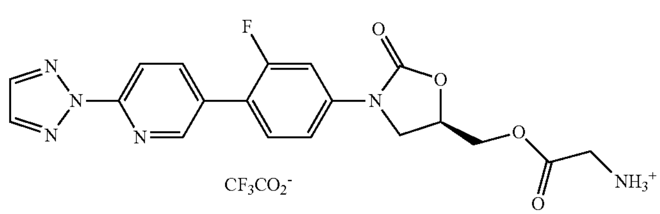 |
| 36 | 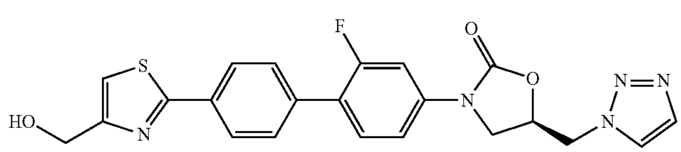 [SMILES: O=C1O[C@@H](Cn2ccnn2)CN1c1ccc(-c2ccc(-c3nc(CO)cs3)cc2)c(F)c1] |

TABLE 1-continued

| Compound | Structure |
|---|---|
| 37 | 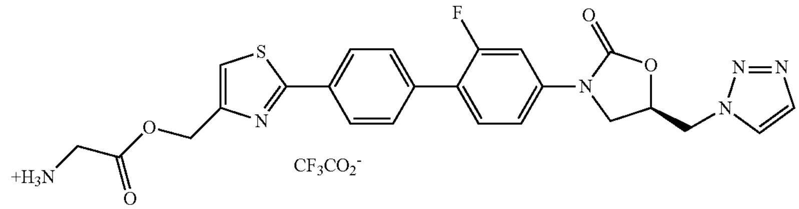 |
| 38 | 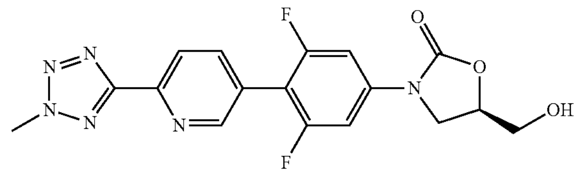 [SMILES: Cn1nnc(-c2ccc(-c3c(F)cc(N4C[C@H](CO)OC4=O)cc3F)cn2)n1] |
| 39 | 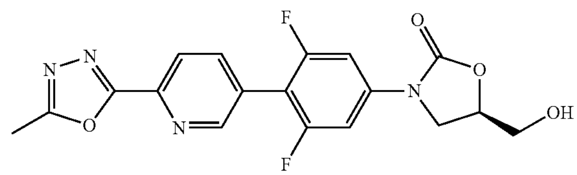 [SMILES: Cc1nnc(-c2ccc(-c3c(F)cc(N4C[C@H](CO)OC4=O)cc3F)cn2)o1] |
| 40 | 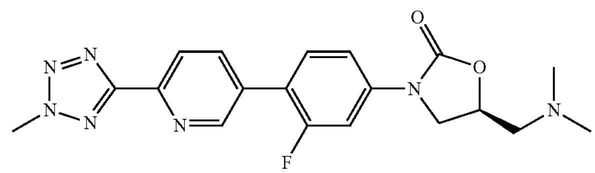 |
| 41 | 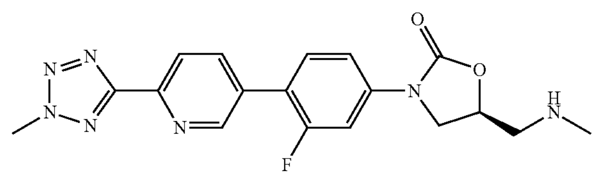 |
| 42 | 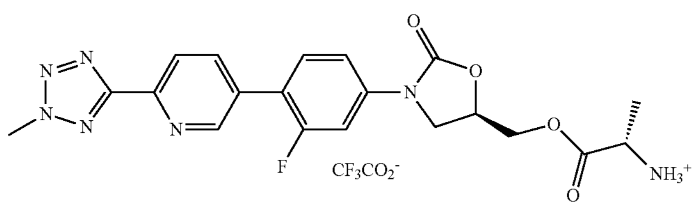 |
| 43 | 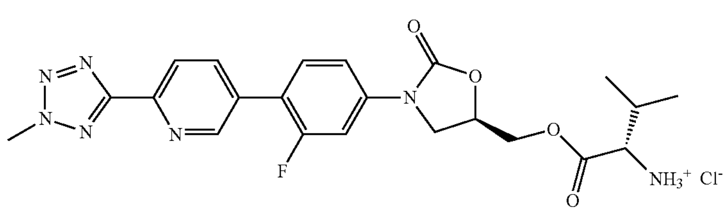 [SMILES: CC(C)[C@H]([NH3+])C(=O)OC[C@H]1CN(c2ccc(-c3ccc(-c4nnn(C)n4)nc3)c(F)c2)C(=O)O1 ; [Cl-]] |
| 44 | 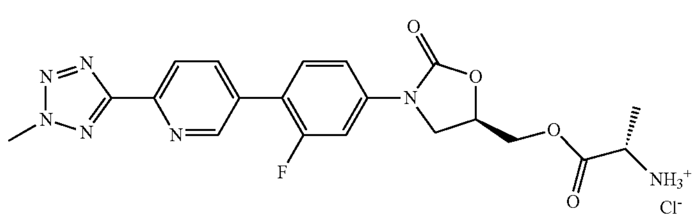 |

TABLE 1-continued

| Compound | Structure |
|---|---|
| 45 | 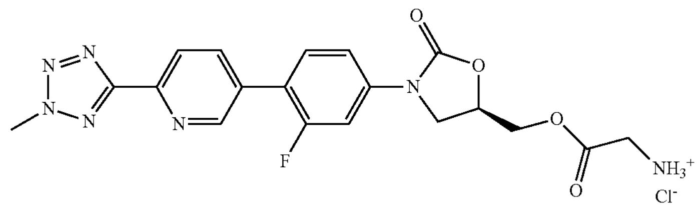 [SMILES: Cn1nnc(-c2ccc(-c3ccc(N4C[C@H](COC(=O)C[NH3+])OC4=O)cc3F)cn2)n1 ; [Cl-]] |
| 46 | 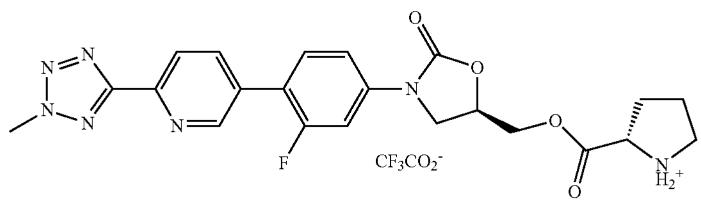 |
| 47 | 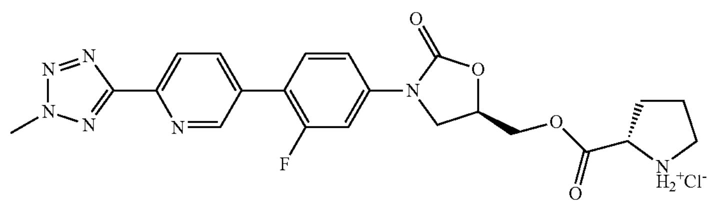 |
| 48 | 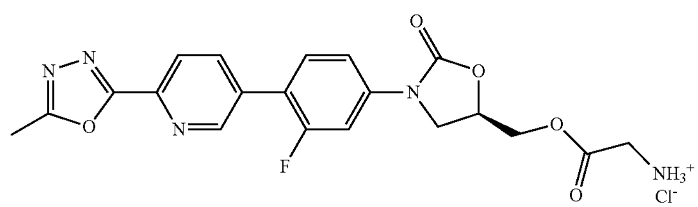 [SMILES: Cc1nnc(-c2ccc(-c3ccc(N4C[C@H](COC(=O)C[NH3+])OC4=O)cc3F)cn2)o1 ; [Cl-]] |
| 49 | 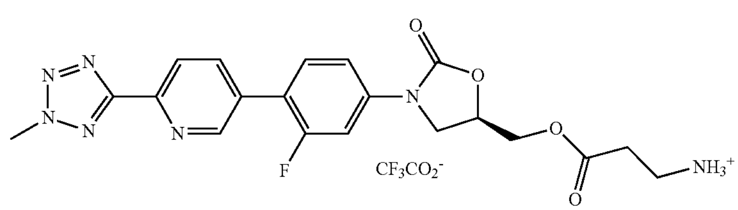 |
| 50 | 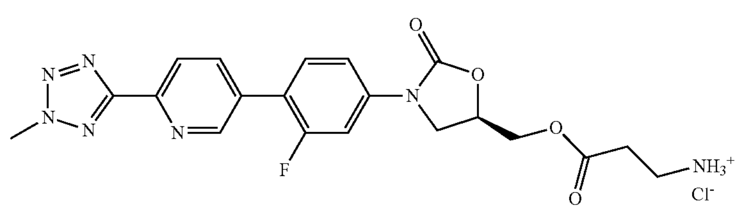 [SMILES: Cn1nnc(-c2ccc(-c3ccc(N4C[C@H](COC(=O)CC[NH3+])OC4=O)cc3F)cn2)n1 ; [Cl-]] |
| 51 | 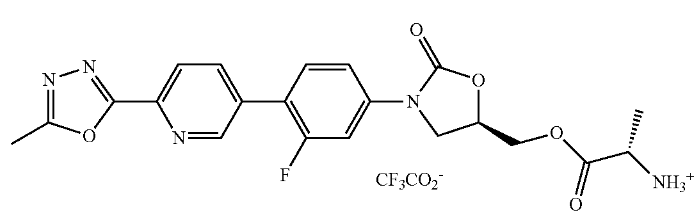 |

TABLE 1-continued

| Compound | Structure |
|---|---|
| 52 | 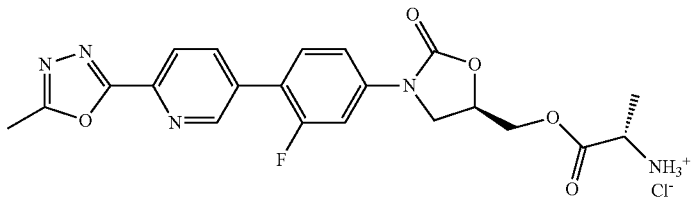 [SMILES: Cc1nnc(-c2ccc(-c3ccc(N4C[C@H](COC(=O)[C@H](C)[NH3+])OC4=O)cc3F)cn2)o1 ; [Cl-]] |
| 53 | 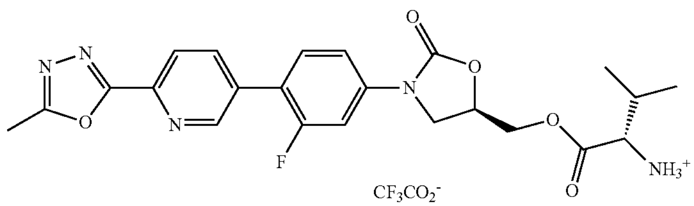 |
| 54 | 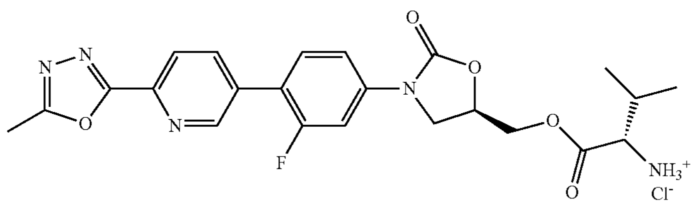 [SMILES: Cc1nnc(-c2ccc(-c3ccc(N4C[C@H](COC(=O)[C@@H]([NH3+])C(C)C)OC4=O)cc3F)cn2)o1 ; [Cl-]] |
| 55 | 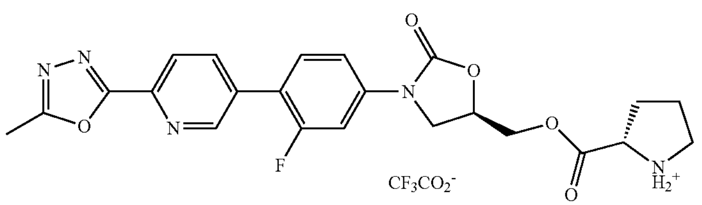 |
| 56 | 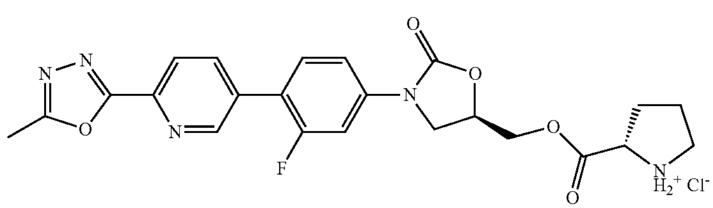 [SMILES: Cc1nnc(-c2ccc(-c3ccc(N4C[C@H](COC(=O)[C@@H]5CCC[NH2+]5)OC4=O)cc3F)cn2)o1 ; [Cl-]] |
| 57 | 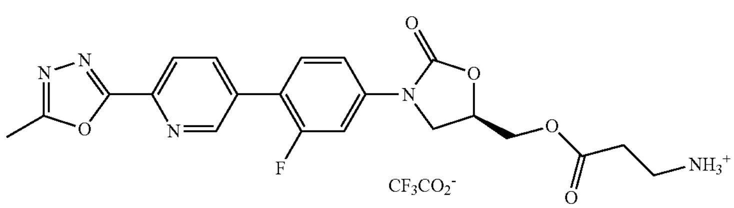 |
| 58 | 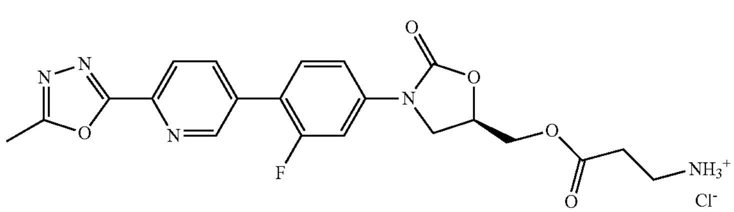 [SMILES: Cc1nnc(-c2ccc(-c3ccc(N4C[C@H](COC(=O)CC[NH3+])OC4=O)cc3F)cn2)o1 ; [Cl-]] |

TABLE 1-continued

| Compound | Structure |
|---|---|
| 59 | 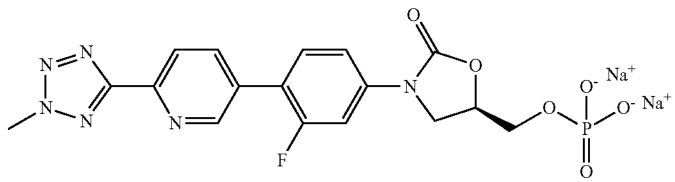 [SMILES: Cn1nnc(-c2ccc(-c3ccc(N4C[C@H](COP(=O)([O-])[O-])OC4=O)cc3F)cn2)n1 ; [Na+] ; [Na+]] |
| 60 | 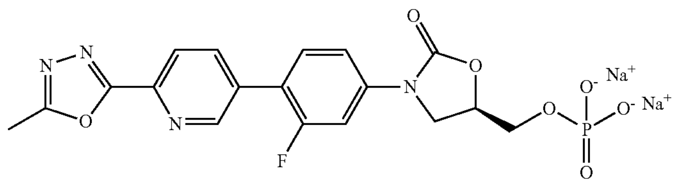 [SMILES: Cc1nnc(-c2ccc(-c3ccc(N4C[C@H](COP(=O)([O-])[O-])OC4=O)cc3F)cn2)o1 ; [Na+] ; [Na+]] |
| 61 | 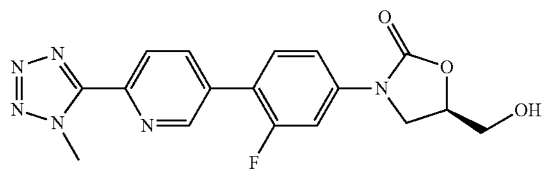 [SMILES: Cn1nnnc1-c1ccc(-c2ccc(N3C[C@H](CO)OC3=O)cc2F)cn1] |
| 62 | 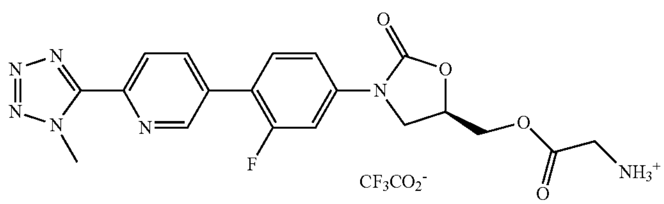 |
| 63 | 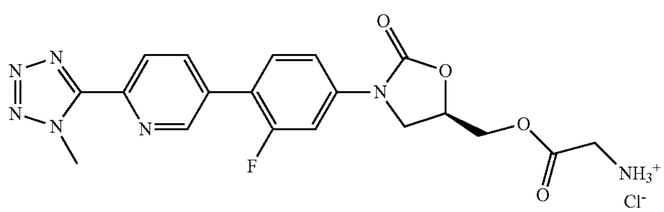 [SMILES: Cn1nnnc1-c1ccc(-c2ccc(N3C[C@H](COC(=O)C[NH3+])OC3=O)cc2F)cn1 ; [Cl-]] |
| 64 | 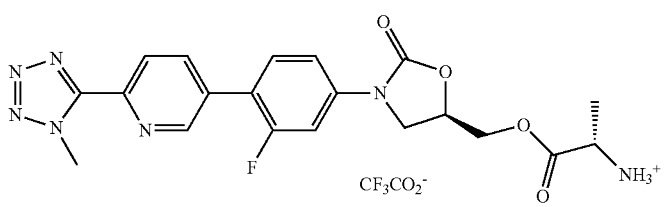 |
| 65 | 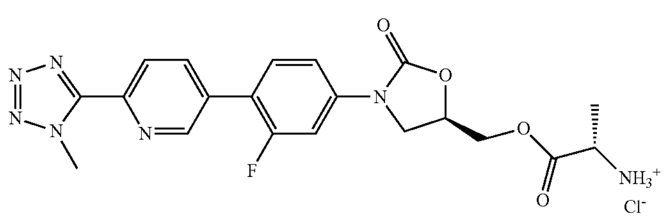 |
| 66 | 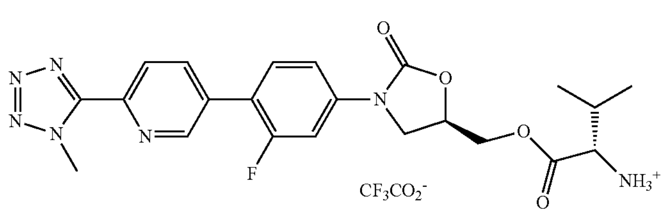 |

TABLE 1-continued
| Compound | Structure |
| --- | --- |
| 67 | 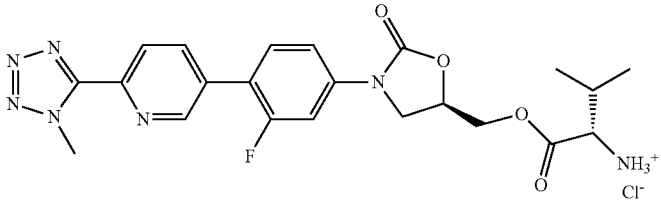 [SMILES: CC(C)[C@H]([NH3+])C(=O)OC[C@H]1CN(c2ccc(-c3ccc(-c4nnnn4C)nc3)c(F)c2)C(=O)O1 ; [Cl-]] |
| 68 | 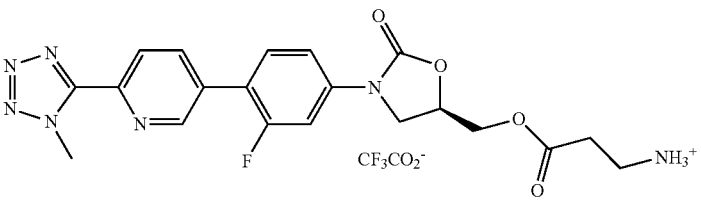 |
| 69 | 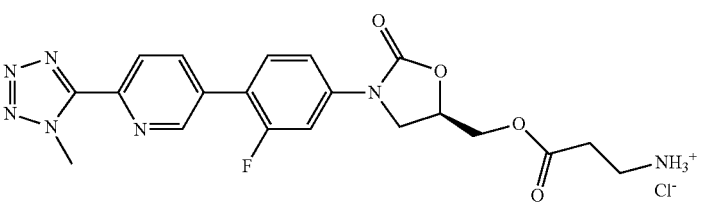 [SMILES: Cn1nnnc1-c1ccc(-c2ccc(N3C[C@H](COC(=O)CC[NH3+])OC3=O)cc2F)cn1 ; [Cl-]] |
| 70 | 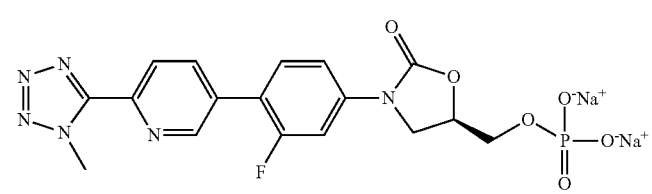 |
| 71 | 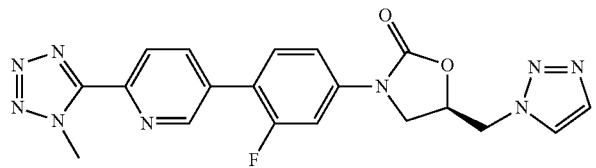 [SMILES: Cn1nnnc1-c1ccc(-c2ccc(N3C[C@H](Cn4ccnn4)OC3=O)cc2F)cn1] |
| 72 | 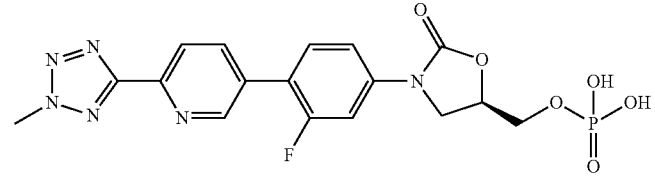 [SMILES: Cn1nnc(-c2ccc(-c3ccc(N4C[C@H](COP(=O)(O)O)OC4=O)cc3F)cn2)n1] |
| 73 | 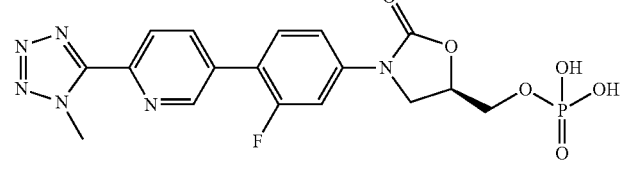 |

For example any of compounds 1-73 described above may be used in the therapeutic combinations described herein.

The protein synthesis inhibitor in the therapeutic combination may include an oxazolidinone derivative of Formula (I), or a pharmaceutically acceptable salt thereof Formula (I)

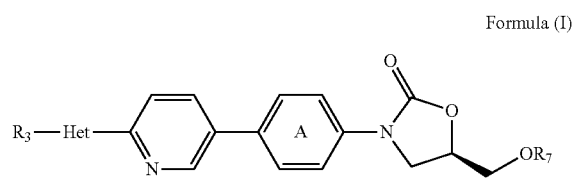

wherein: Het is tetrazole or oxadiazole; ring A is unsubstituted or has at least one fluorine substituent; $R_7$ is H or a prodrug substituent; $R_3$ is hydrogen, $C_{1-4}$ alkyl group that is unsubstituted such as methyl, or substituted with cyano, —$(CH_2)m$-$OR_S$ or ketone; and m is 0, 1, 2, 3, or 4.

The prodrug substituent may be $PO(OH)_2$ or $PO(O)_2^{-2}$ $(M^+)_2$, wherein $M^+$ is a metal cation such as $Na^+$. The protein synthesis inhibitor may have the formula:

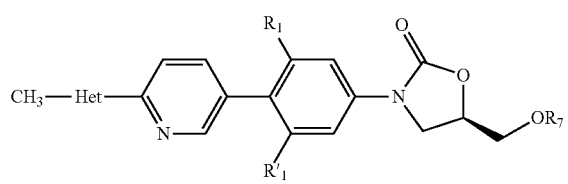

wherein $R_1$ and $R'_1$ may be H or fluorine, such as wherein one of $R_1$ and $R'_1$ may be F (and the other is H). For example, compounds wherein Het is tetrazolyl, may be

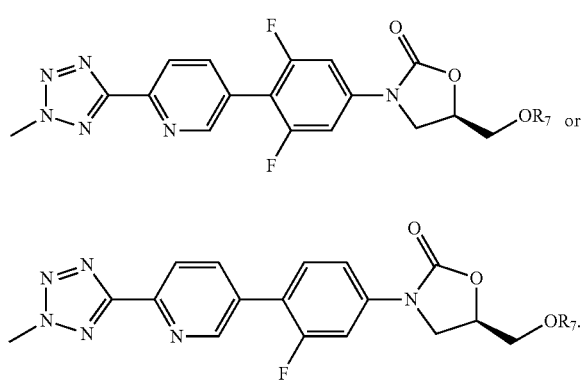

Compounds wherein Het is oxadiazolyl, may be

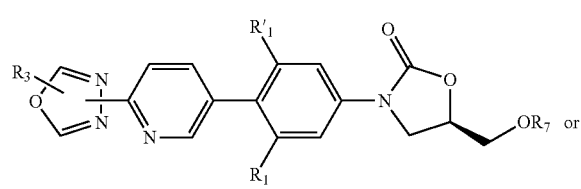

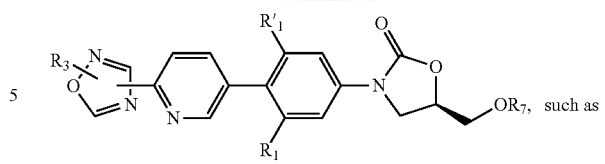

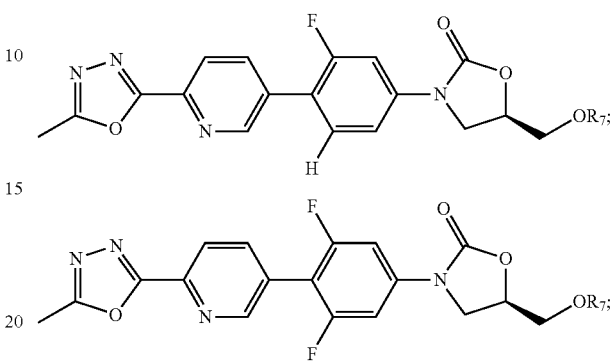

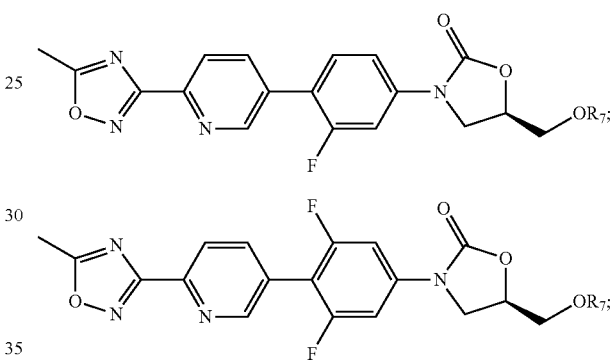

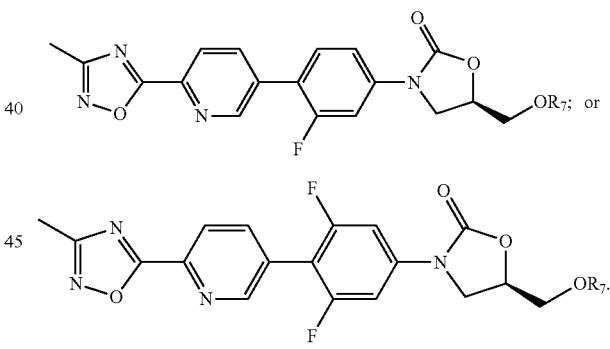

Tedizolid (formerly known as torezolid or TR-700) is the active hydroxymethyl oxazolidinone having the following formula:

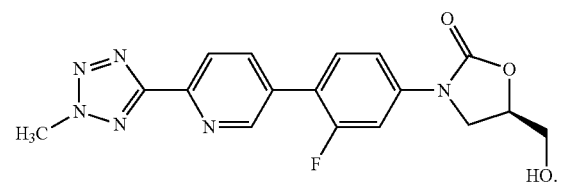 [SMILES: Cn1nnc(-c2ccc(-c3ccc(N4C[C@H](CO)OC4=O)cc3F)cn2)n1]

Pharmaceutical prodrugs such as tedizolid phosphate (also referred to as TR-701, torezolid phosphate, and TR-701 "free acid" or FA) have the following formula:

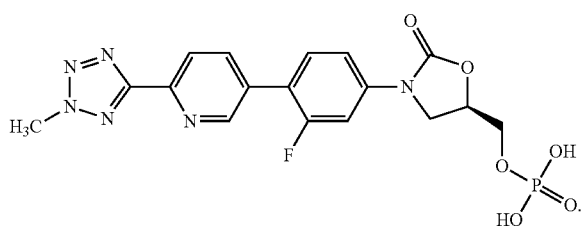 [SMILES: Cn1nnc(-c2ccc(-c3ccc(N4C[C@H](COP(=O)(O)O)OC4=O)cc3F)cn2)n1]

The disodium salt of tedizolid phosphate, has the following structure:

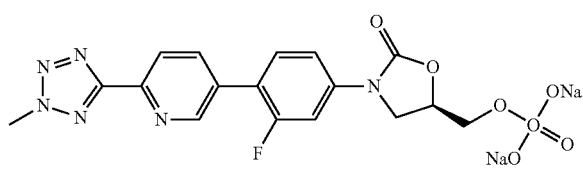

The therapeutic combination comprising daptomycin and the protein synthesis inhibitor herein may indicate the protein synthesis inhibitor specifically in terms of the active moiety "tedizolid;" however, in these cases "tedizolid" includes tedizolid, tedizolid phosphate, or tedizolid disodium salt. Similarly, reference to other active moieties herein include pharmaceutically acceptable variations such as salts, esters and prodrugs of the active moiety.

As is common with pharmaceutical agents, the prophylactic or therapeutic dose of the antibacterial drug used in the treatment of a bacterial infection will vary with the severity of the infection and the route by which the drug is administered. The dose, and perhaps the dose frequency, will also vary according to the age, body weight, and response of the individual patient. Similarly, the dosage of the protein synthesis inhibitor antibiotic can be readily determined to impede the development of resistance to the desired degree.

The optimal dosage of each of the daptomycin and the protein synthesis inhibitor antibiotic can be readily determined by those of skill in the art, and can be defined in a variety of ways. For example, the dosage of the daptomycin may be administered in accordance with known monotherapy administration. According to the prescribing information, which is incorporated herein by reference, daptomycin is supplied as a 500 mg lyophilized powder for reconstitution in a single-use vial. The recommended dosage is 4 mg/kg for complicated skin and skin structure infections and 6 mg/kg for S. aureus bloodstream infections. Nonetheless, other dosages are also contemplated such as no more than about 8 mg/kg, no more than about 7 mg/kg, no more than about 6 mg/kg, no more than about 5 mg/kg, no more than about 4 mg/kg, no more than about 3 mg/kg, no more than about 2 mg/kg, or no more than about 1 mg/kg. For example, dosages of about 1-8 mg/kg, about 3-7 mg/kg, or about 4-6 mg/kg (such as 4 mg/kg or 6 mg/kg) of the patient's body weight are contemplated.

The protein synthesis inhibitor antibiotic can be specified in various ways.

For example, in one embodiment, the protein synthesis inhibitor antibiotic is administered to the patient at a dosage that achieves a concentration in the patient's blood less than the minimum inhibitory concentration (MIC) of the drug for methicillin-resistant Staphylococcus aureus strain NRS123 (also known an MW2). In other embodiments, the dosage achieves a concentration in the patient's blood less than about one-half, and in still other embodiments, less than about one-quarter of the MIC of the drug for methicillin-resistant Staphylococcus aureus strain NRS123.

In other embodiments, the protein synthesis inhibitor antibiotic is administered at a dosage to achieve a $C_{max}$ value of about 10 to 500 µg/mL, or about 1 to 50 µg/mL, or about 0.1 to 5 µg/mL, as desired.

In still other embodiments, the dosage is defined in absolute terms as the weight of the protein synthesis inhibitor antibiotic administered per kilo of body weight in the patient. In this embodiment, the dosage of the protein synthesis inhibitor antibiotic is about 0.01-50 mg/kg, about 0.1-10 mg/kg, or about 0.01-1 mg/kg of the patient's body weight in each case. In some aspects, a daily dosage of the protein synthesis inhibitor antibiotic, e.g., tedizolid, used in the therapeutic combination will be a subclinical level, such as less than a 200 mg clinical dose. Assuming a 70 kg patient, a 200 mg clinical dose equates to approximately 3 mg/kg. Thus, dosages contemplated herein may be about 0.01-5 mg/kg, such as no more than about 5 mg/kg, such as no more than about 4 mg/kg, such as no more than about 3 mg/kg, such as no more than about 2 mg/kg, no more than about 1 mg/kg, no more than about 0.5 mg/kg, no more than about 0.25 mg/kg, or no more than about 0.1 mg/kg. Thus, the dosage form or daily dose may include about 250 mg, 200 mg, 175 mg, 150 mg, 100 mg, 75 mg, 50 mg, 35 mg, 25 mg, 20 mg, 10 mg, or 5 mg of the protein synthesis inhibitor antibiotic, such as tedizolid. Although sub-therapeutic levels of the protein synthesis inhibitor, such as tedizolid, may be used, more pronounced effects may be seen using higher doses in the combination treatment.

With respect to tedizolid, an amount of tedizolid effective to prevent the development of daptomycin non-susceptibility, may include amounts that are above the MIC, such as the standard dosage for tedizolid for treating an infection. For example, a single 200 mg dose of tedizolid, administered as an oral dosage form, such as an oral solution, or intravenously, may be used unless otherwise indicated. Higher doses of tedizolid may also be used, such as 200, 300 or 400 mg. Of course, amounts of tedizolid less than the MIC as described herein may also be used.

Bacterial Species

Bacteria against which the method of the present application can be used include both gram-positive and gram-negative genera. Gram-positive genera against which the method can be used include Staphylococcus, Streptococcus, Enterococcus, Clostridium, Haemophilus, Listeria, Corynebacterium, Bifidobacterium, Eubacterium, Lactobacillus, Leuconostoc, Pediococcus, Peptostreptococcus, Propionibacterium, and Actinomyces.

Particular gram-positive species against which the method can be used include S. aureus (including methicillin-resistant S. aureus), S. epidermidis, S. haemolyticus, S. hominis, S. saprophyticus, S. pneumoniae, S. pyogenes, S. agalactiae, S. avium, S. Bovis, S. lactis, S. sangius, E. faecalis, E. faecium, C. difficile, C. clostridiiforme, C. innocuum, C. perfringens, C. ramosum, L. monocytogenes, C. jeikeium, E. aerofaciens, E. lentum, L. acidophilus, L. casei, L. plantarum, P. anaerobius, P. asaccarolyticus, P. magnus, P. micros, P. prevotil, P. productus, and P. acnes.

Clinically the salient pathogens include positive species against which the method can be used include S. aureus (including methicillin-resistant S. aureus), S. epidermidis, S. haemolyticus, S. pneumoniae, S. pyogenes, S. agalactiae, E. faecalis, E. faecium, C. difficile, C. clostridiiforme, C. perfringens, and L. monocytogenes.

Non-Susceptibility

Diminished susceptibility developed during daptomycin therapy is well documented. See e.g., Cubicin® (daptomycin for injection) for the treatment of *Staphylococcus aureus* bacteremia, including those with known or suspected infective endocarditis, FDA Briefing Document for Anti-Infective Drugs Advisory Committee Meeting, Mar. 6, 2006. Preventing the development of daptomycin non-susceptibility, may refer to bacteria having reduced susceptibility that may be caused by genetic mutations in genes, such as mprF, yycF/yycG, rpoB, and rpoC, or other factors, such as cell wall thickening, permeability or a change in cell surface charge, that reduce the ability of daptomycin to effectively kill bacteria selected over the course of treatment of the bacterial infection. Factors that reduce susceptibility to daptomycin have been studied in the literature. Cui, et al., Antimicrobial Agents and Chemotherapy, 50:3, 1079-82 (2006); Silverman et al., Antimicrobial Agents and Chemotherapy, 45:6 1799-1802 (2001); Friedman, et al., Antimicrobial Agents and Chemotherapy, 50:6 2137-45 (2006); Firsov et al., Journal of Antimicrobial Chemotherapy 58, 1185-92 (2006).

In some aspects, the development of daptomycin non-susceptibility is prevented such that the infection is cleared in patient before administration of high and toxic levels of daptomycin would be needed.

In some aspects, the phrase "prevent the development of non-susceptibility of daptomycin non-susceptibility in bacteria" or similar use of the word "preventing" refers both to preventing non-susceptibility as well as reducing the fold increase in MIC value of daptomycin compared to daptomycin alone. Thus, in some aspects, non-susceptibility may not be completely prevented but the presence of the protein synthesis inhibitor, such as tedizolid, may prolong the efficacy of daptomycin in a clinical setting.

Daptomycin-Susceptible Bacterium

Development of resistance to daptomycin becomes most pronounced after extended administration. In some aspects, methods to prevent daptomycin resistance or non-susceptibility are useful if the bacteria are susceptible to daptomycin therapy. Optimally, the bacteria remain susceptible to daptomycin until the infection is resolved. Thus, the therapeutic combination may be administered for as much as two, four, six weeks, or more as determined by the treating physician. In some aspects, daptomycin-susceptible bacterium are pathogens demonstrating MIC values of less than or equal to 1 µg/ml, for example 0.5 µg/ml or 0.025 µg/ml. Preventing the emergence of daptomycin non-susceptibility is valuable if a window remains that is large enough to resolve the infection before resistance or non-susceptibility can develop. Bacterium demonstrating MIC values of 4 µg/ml or greater, including greater than 8, 16 or 32 µg/ml may be considered nonsusceptible to daptomycin.

Mechanism of the Protein Synthesis Inhibitor

Without being bound by theory, in some instances it is believed that the protein synthesis inhibitor may act through binding to a ribosome, a tRNA synthetase, a translation factor including but not limited to an elongation factor, an initiation factor or a termination factor.

Also, without being bound by theory, the inhibition of bacterial protein synthesis might impede the synthesis of the physiological machinery to either transport daptomycin out of the bacterial cell, reduce the uptake of daptomycin into the bacterial cell, or to modify daptomycin enzymatically and reduce its toxicity to the bacterium. Protein synthesis inhibitors may also be responsible for inhibiting the production or recycling of proteins that reduce susceptibility of daptomycin.

Pharmaceutical Formulations

Those skilled in the art will appreciate that a variety of prodrugs, salts, hydrates, solvates, and polymorphs of the compounds disclosed herein are available or may be produced, and various isotopically-substituted variants (through, e.g., substitution of deuterium for hydrogen, $^{13}$C for carbon, $^{15}$N for nitrogen, or $^{32}$P for phosphorus) can also be readily produced. All such derivatives are contemplated within the scope of this disclosure. In addition, an active moiety or antibiotic recited herein includes any such variations although not specifically mentioned.

The daptomycin or the protein synthesis inhibitor antibiotic may be in the form of a pharmaceutical composition comprising one or more physiologically acceptable surface active agents, additional carriers, diluents, excipients, smoothing agents, suspension agents, film forming substances, and coating assistants, or a combination thereof. Acceptable additional carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, microcrystalline cellulose, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of daptomycin or the protein synthesis inhibitor antibiotic disclosed herein with other chemical components, such as diluents or additional carriers. The pharmaceutical composition facilitates administration of the daptomycin or the protein synthesis inhibitor antibiotic to an organism. Multiple techniques of administering a pharmaceutical composition exist in the art including, but not limited to, oral, injection, aerosol, parenteral, and topical administration.

Pharmaceutical compositions of daptomycin for injection are commercially available. According to the full prescribing information, a daptomycin-containing lyophilized powder is reconstituted with 0.9% sodium chloride for injection to form a reconstituted solution.

Pharmaceutical compositions of tedizolid may also be obtained by reacting the free acid dihydrogen phosphate with inorganic or organic bases such as sodium hydroxide or magnesium hydroxide. In some embodiments, pharmaceutically acceptable salts of the compounds disclosed herein (e.g., as made in situ during the manufacture of an intravenous formulation) are provided. Exemplary compositions for lyophilization and injection may be found in US Publication No. 20100227839. For example, tedizolid phosphate formulated in situ as the disodium salt using sodium hydroxide. A compounding solution for lyophilization was prepared containing mannitol as a bulking agent, sodium hydroxide for in situ salt formation, hydrochloric acid for pH adjustment and water as a manufacturing solvent, which is removed during lyophilization. For instance, a vial of the lyophilized composition may contain 200 mg/vial dose of tedizolid phosphate. The lyophilized material may be reconstituted, for example with 0.9% sodium chloride for injection, water for injection, or D5W (5% dextrose and water for injection).

It is contemplated that the combination of daptomycin and protein synthesis inhibitor such as tedizolid phosphate may be lyophilized in the same vial. In some aspects, each component may be reconstituted separately and then combined in the same intravenous infusion bag or kept separate in different intravenous infusion bags. Generally, the components may be delivered at about the same time but may be administered sequentially with up to about 2 hours between administrations of each component.

The term "carrier" refers to a chemical compound that facilitates the incorporation of daptomycin or the protein synthesis inhibitor antibiotic into cells or tissues.

The term "diluent" refers to chemical compounds diluted in water that will dissolve the composition of interest as well as stabilize the biologically active form of the daptomycin or the protein synthesis inhibitor antibiotic. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. As used herein, an "excipient" refers to an inert substance that is added to a composition to provide, without limitation, bulk, consistency, stability, binding ability, lubrication, disintegrating ability, etc., to the composition. A "diluent" is a type of excipient.

The term "physiologically acceptable" refers to a carrier or diluent that does not abrogate the biological activity and properties of the compound.

The pharmaceutical compounds of daptomycin or the protein synthesis inhibitor antibiotic described herein can be administered to a human patient per se, or in pharmaceutical compositions where they are mixed with other active ingredients, as in combination therapy, or suitable carriers or excipient(s). In some embodiments, a dosage form includes those forms in which the compound is administered per se. In addition, a dosage form may include a pharmaceutical composition. In any case, the dosage form may comprise a sufficient amount of daptomycin or the protein synthesis inhibitor antibiotic to treat a bacterial infection as part of a particular administration protocol, as would be understood by those of skill in the art. Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The daptomycin or the protein synthesis inhibitor antibiotic can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions may be manufactured in a manner that is itself known, e.g., by means of conventional mixing, dissolving, granulating, dragee-making, levigating, emulsifying, encapsulating, entrapping or tabletting processes.

Pharmaceutical compositions may be formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, diluents, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, a composition can be formulated readily by combining the compositions of interest with pharmaceutically acceptable carriers well known in the art. Such carriers, which may be used in addition to the cationic polymeric carrier, enable the compositions of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP), e.g., Povidone. If desired, disintegrating agents may be added, such as the cross-linked polyvinylpyrrolidone (e.g. Crospovidone), agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in a conventional manner.

For administration by inhalation, the composition can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compositions may also be formulated in rectal compositions such as suppositories or retention enemas, e.g., containing conventional suppository bases such as cocoa butter or other glycerides.

In addition to the formulations described previously, the compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Methods for treating bacterial infections may include administering a therapeutically effective amount of the daptomycin, such as an antibacterially effective amount, and the protein synthesis inhibitor antibiotic as described herein useful for preventing daptomycin non-susceptibility. Treating a bacterial infection may also include prophylactically administering the combination to prevent infection or the spread of an infection in a subject at imminent risk of infection, such as a subject receiving or about to undergo surgery, an immunocompromised subject, or subject otherwise at risk of an infection if the compound was not administered. The combination therapy of daptomycin and the protein synthesis inhibitor antibiotic shows inhibitory activity against a broad spectrum of bacteria, against methicillin-resistant *Staphylococcus aureus* (MRSA) and vancomycin resistant *Enterococcus* (VRE) and have excellent relative antibiotic activity with a relatively low concentration thereof or in vivo. Further, the combination therapy of daptomycin and the protein synthesis inhibitor antibiotic may exert potent antibacterial activity against various human and animal pathogens, including gram-positive bacteria such as *Staphylococcus, Enterococcus* and *Streptococcus*, anaerobic microorganisms such as *Bacteroides* and Clostridia, and acid-resistant microorganisms such as *Mycobacterium tuberculosis* and *Mycobacterium avium*. In an embodiment, the bacterial infection that may be treated or ameliorated is MRSA.

The compositions or pharmaceutical compositions described herein may be administered to the subject by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; as well as (d) administration topically; as deemed appropriate by those of skill in the art for bringing the combination therapy of daptomycin and the protein synthesis inhibitor antibiotic into contact with living tissue.

Pharmaceutical compositions suitable for administration include compositions where the active ingredients are contained in an amount effective to achieve its intended purpose. In some embodiments, a therapeutically effective amount of daptomycin is an amount effective to treat a bacterial infection, for example, in a mammalian subject (e.g., a human).

The therapeutically effective amount of the combination therapy of daptomycin and the protein synthesis inhibitor antibiotic disclosed herein required as doses will depend on the route of administration, the type of animal, including human, being treated, and the physical characteristics of the specific animal under consideration. The doses can be tailored to achieve a desired effect, but will depend on such factors as weight, diet, concurrent medication and other factors which those skilled in the medical arts will recognize. More specifically, a therapeutically effective amount means an amount of daptomycin effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical trial applications of products are commenced at lower dosage levels, with dosage level being increased until the desired effect is achieved with an appropriate balance of efficacy and safety as determined by one skilled in the art. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or until adverse side effects disappear. The dosage may range broadly, depending upon the desired effects and the therapeutic indication. Typically, dosages may be about 0.01 microgram/kg to about 50 mg/kg body weight, preferably about 0.5 microgram/kg to about 10 mg/kg body weight. Alternatively dosages may be based and calculated upon the surface area of the patient, as understood by those of skill in the art.

The exact formulation, route of administration and dosage for the pharmaceutical compositions of the combination therapy of daptomycin and the protein synthesis inhibitor antibiotic can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). In some embodiments, the dose range of the daptomycin administered to the patient can be from about 0.1 to about 100 mg/kg of the patient's body weight, for example 0.5 to 20 mg/kg, 0.5 to 10 mg/kg, or 0.5 to 5 mg/kg. In some embodiments, the dose range of the protein synthesis inhibitor antibiotic administered to the patient can be from about 0.1 to about 100 mg/kg of the patient's body weight, for example 0.5 to 20 mg/kg, 0.5 to 10 mg/kg, or 0.5 to 5 mg/kg. Each dosage may be a single one or a series of two or more given in the course of one or more days, as is needed by the patient. In instances where human dosages for daptomycin or the protein synthesis inhibitor antibiotic have been established for at least some conditions, the same dosages, or dosages that are about 0.1% to about 500%, more preferably about 25% to about 250% of the established human dosage may be used. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. An intravenous, subcutaneous, or intramuscular dose of the active ingredient of about 0.01 mg/kg to about 50 mg/kg, preferably about 0.1 mg/kg to about 60 mg/kg, e.g. about 1 to about 40 mg/kg is used. In cases of administration of a pharmaceutically acceptable salt, dosages may be calculated as the free acid. In some embodiments, the composition is administered 1 to 4 times per day. Alternatively the compositions may be administered by continuous intravenous infusion, preferably at a dose of up to about 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety, such as daptomycin, which are sufficient to maintain the antibiotic effects, or minimal effective concentration (MEC). The MEC will vary for each compound but can be estimated from in vitro data. Dosages necessary to achieve the MEC will depend on individual characteristics and route of administration.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered may be dependent on the subject being treated, on the subject's weight, the severity of the infection, the manner of administration and the judgment of the prescribing physician.

Compositions disclosed herein can be evaluated for efficacy and toxicity using known methods. For example, the toxicology of the compound may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The combination therapy of daptomycin and the protein synthesis inhibitor antibiotic, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound formulated in a compatible pharmaceutical carrier may also be prepared, placed in an appropriate container, and labeled for treatment of an indicated condition.

The terms "approximately, "about," and "substantially" as used herein represent an amount close to the stated amount that still performs the desired function or achieves the desired result. For example, the terms "approximately," "about" and "substantially" may refer to an amount that is within less than 10% of, within less than 5% of, within less than 1% of, within less than 0.1% of, and within less than 0.01% of the stated amount.

EXAMPLES

Example 1

*S. aureus* strains MW2 (NARSA collection clinical MRSA isolate, NRS123) and ATCC 33591 (MRSA strain from the American Type Culture Collection) were cultured on Mueller-Hinton II cation adjusted (MHA) medium in 90×90 mm square petri dishes. MHA containing ¼ of the MIC value of TR-700, TR-705, LZD, TIA, CLI, TET, or VAN, TMP/SMX throughout the plate and a continuous linear gradient of DAP across the plate was used to passage MW2. ATCC 33591 was passaged with ¼ of the MIC of a subset of these drugs (TR-700, TMP/SMX, and VAN). A DAP-only control passage group was included for both strains. DAP gradients were created by pouring two layers of media as previously described (Bryson, V., et al. 1952. Microbial selection. Science 116:45-51; Locke, J. B., et al., 2009. Antimicrob. Agents Chemother. 53:5265-5274). Following each passage the leading edge of growth (i.e., most resistant cells) was resuspended in phosphate buffered saline (PBS) to an absorbance of 0.30 $OD_{600}$ and a 100 µl aliquot containing ~$3.0×10^7$ CFU (colony-forming units) was spread on to the proceeding passage plate. The starting maximal DAP concentration was 2 µg/ml and was increased in two-fold increments when the leading edge of growth surpassed the half way point on the plate. A glycerol stock was made from the total cell population for each culture condition for each passage. Thirty serial passages were completed for each treatment group. MIC testing (broth microdilution; CLSI. 2009. M07-A8. Methods for dilution antimicrobial susceptibility tests for bacteria that grow aerobically; approved standard, 8th ed. Clinical and Laboratory Standards Institute, Wayne, Pa.) was performed on total cell populations for each group every fifth passage using all selecting agents and values are listed in Tables 2 and 3 below.

TABLE 2

| Passage | Selection group | MIC (µg/ml) | | | | | | | | |
|---|---|---|---|---|---|---|---|---|---|---|
| | | DAP | TR-700 | TR-705 | LZD | TIA | CLI | TET | TMP/SMX | VAN |
| 0 | NRS123 WT | 0.25 | 0.5 | 0.5 | 2 | 0.5 | 0.125 | 0.5 | 0.125/2.38 | 1 |
| 5 | DAP | 1 | 0.5 | 0.5 | 2 | 0.5 | 0.125 | 0.25 | 0.125/2.38 | 2 |
| | DAP + TR-700 | 0.5 | 0.5 | 0.5 | 2 | 1 | 0.125 | 0.5 | 0.125/2.38 | 2 |
| | DAP + TR-705 | 1 | 0.5 | 0.5 | 2 | 1 | 0.0625 | 0.5 | 0.0625/1.19 | 4 |
| | DAP + LZD | 1 | 0.5 | 0.5 | 2 | 1 | 0.0625 | 0.5 | 0.125/2.38 | 4 |
| | DAP + TIA | 2 | 0.5 | 0.5 | 2 | 0.5 | 0.125 | 0.5 | 0.125/2.38 | 2 |
| | DAP + CLI | 1 | 0.5 | 0.5 | 2 | 1 | 0.0625 | 0.5 | 0.125/2.38 | 4 |
| | DAP + TET | 1 | 0.5 | 0.5 | 2 | 0.5 | 0.125 | 0.25 | 0.125/2.38 | 2 |
| | DAP + TMP/SMX | 4 | 0.25 | 0.25 | 1 | 0.5 | 0.125 | 0.125 | 0.25/4.75 | 8 |
| | DAP + VAN | 1 | 0.25 | 0.25 | 1 | 0.5 | 0.125 | 0.25 | 0.25/4.75 | 4 |
| 10 | DAP | 2 | 0.5 | 0.5 | 2 | 0.5 | 0.125 | 0.125 | 0.125/2.38 | 4 |
| | DAP + TR-700 | 1 | 0.5 | 0.5 | 2 | 1 | 0.125 | 0.5 | 0.125/2.38 | 2 |
| | DAP + TR-705 | 1 | 0.5 | 0.5 | 2 | 0.5 | 0.125 | 0.125 | 0.0625/1.19 | 2 |
| | DAP + LZD | 4 | 0.5 | 0.5 | 2 | 1 | 0.0625 | 0.25 | 0.125/2.38 | 8 |
| | DAP + TIA | 4 | 0.5 | 0.5 | 2 | 0.5 | 0.125 | 0.25 | 0.125/2.38 | 4 |
| | DAP + CLI | 4 | 0.5 | 0.5 | 2 | 1 | 0.0625 | 0.5 | 0.125/2.38 | 4 |
| | DAP + TET | 1 | 0.5 | 0.5 | 2 | 0.5 | 0.0625 | 0.5 | 0.125/2.38 | 2 |
| | DAP + TMP/SMX | 2 | 0.5 | 0.5 | 2 | 1 | 0.125 | 0.5 | 0.25/4.75 | 8 |
| | DAP + VAN | 2 | 0.25 | 0.25 | 1 | 0.5 | 0.0625 | 0.25 | 0.25/4.75 | 4 |
| 15 | DAP | 8 | 0.25 | 0.5 | 1 | 0.5 | 0.125 | 0.25 | 0.25/4.75 | 8 |
| | DAP + TR-700 | 1 | 0.5 | 0.5 | 2 | 1 | 0.125 | 0.25 | 0.125/2.38 | 2 |
| | DAP + TR-705 | 2 | 0.5 | 0.5 | 2 | 0.5 | 0.0625 | 0.25 | 0.125/2.38 | 2 |
| | DAP + LZD | 8 | 0.5 | 0.5 | 2 | 1 | 0.125 | 0.25 | 0.25/4.75 | 8 |
| | DAP + TIA | 8 | 0.5 | 0.5 | 2 | 0.5 | 0.0625 | 0.25 | 0.125/2.38 | 4 |
| | DAP + CLI | 8 | 0.25 | 0.5 | 2 | 0.5 | 0.0625 | 0.125 | 0.125/2.38 | 8 |
| | DAP + TET | 2 | 0.25 | 0.25 | 1 | 0.25 | 0.0313 | 0.5 | 0.125/2.38 | 0.5 |
| | DAP + TMP/SMX | 2 | 0.5 | 0.5 | 2 | 1 | 0.125 | 0.25 | 0.25/4.75 | 8 |
| | DAP + VAN | 4 | 0.5 | 0.25 | 1 | 0.5 | 0.125 | 0.25 | 0.25/4.75 | 8 |
| 20 | DAP | 16 | 0.5 | 0.25 | 2 | 0.5 | 0.0625 | 0.125 | 0.25/4.75 | 8 |
| | DAP + TR-700 | 2 | 0.5 | 0.5 | 2 | 1 | 0.125 | 0.25 | 0.125/2.38 | 2 |

TABLE 2-continued

| Passage | Selection group | MIC (μg/ml) | | | | | | | | |
|---|---|---|---|---|---|---|---|---|---|---|
| | | DAP | TR-700 | TR-705 | LZD | TIA | CLI | TET | TMP/SMX | VAN |
| | DAP + TR-705 | 2 | 0.5 | 0.5 | 2 | 0.5 | 0.0625 | 0.125 | 0.25/4.75 | 2 |
| | DAP + LZD | 8 | 0.5 | 0.5 | 2 | 1 | 0.125 | 0.25 | 0.25/4.75 | 8 |
| | DAP + TIA | 8 | 0.5 | 0.5 | 2 | 0.5 | 0.0625 | 0.25 | 0.125/2.38 | 4 |
| | DAP + CLI | 16 | 0.25 | 0.25 | 2 | 0.5 | 0.0625 | 0.125 | 0.125/2.38 | 8 |
| | DAP + TET | 4 | 0.25 | 0.25 | 1 | 0.25 | 0.0313 | 0.25 | 0.125/2.38 | 1 |
| | DAP + TMP/SMX | 2 | 0.5 | 0.5 | 2 | 0.5 | 0.125 | 0.25 | 0.25/4.75 | 8 |
| | DAP + VAN | 8 | 0.5 | 0.25 | 1 | 0.5 | 0.125 | 0.25 | 0.25/4.75 | 8 |
| 25 | DAP | 32 | 0.25 | 0.25 | 1 | 0.25 | 0.125 | 0.125 | 0.25/4.75 | 4 |
| | DAP + TR-700 | 2 | 0.5 | 0.5 | 2 | 1 | 0.125 | 0.25 | 0.125/2.38 | 2 |
| | DAP + TR-705 | 2 | 0.5 | 0.5 | 2 | 0.5 | 0.0625 | 0.125 | 0.125/2.38 | 2 |
| | DAP + LZD | 16 | 0.25 | 0.25 | 1 | 0.25 | 0.0625 | 0.25 | 0.25/4.75 | 8 |
| | DAP + TIA | 8 | 0.5 | 0.5 | 2 | 0.5 | 0.0625 | 0.25 | 0.125/2.38 | 2 |
| | DAP + CLI | 16 | 0.25 | 0.5 | 2 | 0.5 | 0.0625 | 0.125 | 0.125/2.38 | 8 |
| | DAP + TET | 8 | 0.25 | 0.25 | 1 | 0.25 | 0.0313 | 0.25 | 0.125/2.38 | 1 |
| | DAP + TMP/SMX | 4 | 0.25 | 0.25 | 2 | 0.5 | 0.125 | 0.25 | 0.25/4.75 | 8 |
| | DAP + VAN | 8 | 0.25 | 0.25 | 1 | 0.5 | 0.125 | 0.25 | 0.25/4.75 | 8 |
| 30 | DAP | 32 | 0.25 | 0.25 | 1 | 0.25 | 0.125 | 0.25 | 0.25/4.75 | 2 |
| | DAP + TR-700 | 2 | 0.5 | 0.5 | 2 | 0.5 | 0.125 | 0.5 | 0.125/2.4 | 2 |
| | DAP + TR-705 | 4 | 0.5 | 0.5 | 2 | 0.5 | 0.125 | 0.25 | 0.125/2.38 | 2 |
| | DAP + LZD | 32 | 0.5 | 0.5 | 2 | 0.5 | 0.0625 | 0.25 | 0.125/2.38 | 4 |
| | DAP + TIA | 8 | 0.5 | 0.5 | 2 | 0.5 | 0.125 | 0.5 | 0.125/2.38 | 4 |
| | DAP + CLI | 16 | 0.25 | 0.5 | 2 | 0.25 | 0.0625 | 0.25 | 0.25/4.75 | 8 |
| | DAP + TET | 8 | 0.25 | 0.25 | 1 | 0.25 | 0.0313 | 0.5 | 0.125/2.38 | 1 |
| | DAP + TMP/SMX | 4 | 0.5 | 0.5 | 2 | 0.5 | 0.125 | 0.5 | 0.25/4.75 | 8 |
| | DAP + VAN | 8 | 0.25 | 0.25 | 2 | 0.25 | 0.0625 | 0.5 | 0.25/4.75 | 4 |

TABLE 3

| Passage | Selection group | MIC (μg/ml) | | | |
|---|---|---|---|---|---|
| | | DAP | TR-700 | TMP/SMX | VAN |
| 0 | ATCC 33591 WT | 0.5 | 0.5 | 0.5/9.5 | 2 |
| 5 | DAP | 2 | 0.125 | 0.5/9.5 | 4 |
| | DAP + TR-700 | 0.5 | 0.5 | 0.5/9.5 | 2 |
| | DAP + TMP/SMX | 1 | 0.5 | 2/38 | 4 |
| | DAP + VAN | 0.5 | 0.5 | 0.5/9.5 | 4 |
| 10 | DAP | 4 | 0.125 | 0.5/9.5 | 4 |
| | DAP + TR-700 | 1 | 0.5 | 0.5/9.5 | 4 |
| | DAP + TMP/SMX | 2 | 0.25 | 1/19 | 8 |
| | DAP + VAN | 2 | 0.5 | 0.5/9.5 | 4 |
| 15 | DAP | 8 | 0.125 | 0.5/9.5 | 4 |
| | DAP + TR-700 | 1 | 0.5 | 0.5/9.5 | 4 |
| | DAP + TMP/SMX | 4 | 0.25 | 1/19 | 4 |
| | DAP + VAN | 4 | 0.25 | 0.5/9.5 | 4 |
| 20 | DAP | 8 | 0.125 | 0.5/9.5 | 4 |
| | DAP + TR-700 | 2 | 0.5 | 0.5/9.5 | 4 |
| | DAP + TMP/SMX | 4 | 0.25 | 1/19 | 4 |
| | DAP + VAN | 4 | 0.5 | 0.5/9.5 | 8 |
| 25 | DAP | 16 | 0.125 | 0.5/9.5 | 4 |
| | DAP + TR-700 | 4 | 0.25 | 0.5/9.5 | 4 |
| | DAP + TMP/SMX | 8 | 0.25 | 2/38 | 4 |
| | DAP + VAN | 8 | 0.25 | 0.5/9.5 | 8 |
| 30 | DAP | 16 | 0.125 | 0.5/9.5 | 4 |
| | DAP + TR-700 | 4 | 0.5 | 0.5/9.5 | 2 |
| | DAP + TMP/SMX | 8 | 0.25 | 2/38 | 4 |
| | DAP + VAN | 8 | 0.5 | 0.5/9.5 | 4 |

In addition, the DAP MIC values are separately plotted graphically in FIGS. 1 and 2 for both strains.

All serial passage conditions resulted in the selection of DAP$^{ns}$ S. aureus populations by passage 20 (Tables 2, 3). Over the course of the serial passage, DAP MIC values increased 128-fold (0.25 to 32 μg/ml) for MW2 and 32-fold (0.5 to 16 μg/ml) for ATCC 33591 in the DAP-only control groups. All co-selecting groups, with the exception of LZD, resulted in some level of decreased emergence of DAP$^{ns}$ strains by passage 30 (FIGS. 1, 2). Although co-selection with VAN had an effect on preventing the emergence of DAP$^r$ strains in both backgrounds, DAP/VAN cross-resistance was observed as has been previously described (Sakoulas, G., et al. 2006. Antimicrob. Agents Chemother. 50: 1581-1585). Of the ¼ MIC combination groups TR-700 resulted in the smallest fold shift increase in DAP MIC values for MW2 (0.25 to 2 μg/ml) and for ATCC 33591 (0.5 to 4 μg/ml). In the MW2 passage, the TR-705 co-selection group behaved near identically to TR-700 up until P30 where the DAP MIC increased to 4 μg/ml, an equivalent DAP MIC value to the next most efficacious co-selection group, TMP/SMX LZD did not prevent the emergence of DAP non-susceptibility through co-selection at ¼ MIC in MW2, consistent with observations made in a similar S. aureus LZD/DAP combination serial passage study (Berti, A., et al. 2012. Antimicrob. Agents Chemother. 56:5046-53).

Example 2

Test articles of stock solutions of daptomycin (Cubist, lot MCB2007) and TR-700 were prepared at 40 times the final target concentration in DMSO:water (1:1). DMSO was added first, the solutions were allowed to stand for 60 minutes and then the water was added. TR-700 formed a precipitate above 1280 μg/ml; therefore, this was the highest concentration used. Daptomycin was in solution at the concentrations used. The final DMSO concentration was 2.5%. The final drug concentrations in the FIC assay plates were set to bracket the MIC value of each test article for each test organism, unless the strain was totally resistant to the test article.

The test organisms were originally received from clinical sources, or from the American Type Culture Collection. Upon receipt in our laboratory, the isolates were streaked onto the appropriate growth medium: Tryptic Soy Agar II (Becton Dickinson, Sparks, Md.) supplemented with 5% defibrinated sheep blood for streptococci, and unsupplemented Tryptic Soy Agar II for all other organisms. Colonies were harvested from these plates and a cell suspension was prepared in Tryptic Soy Broth (Becton Dickinson) containing cryoprotectant. Aliquots were then frozen at −80° C. On the day prior to assay, the frozen seeds of the organisms to be tested in that session were thawed and streaked for isolation onto the appropriate agar medium plates and incubated overnight at 35° C. The test organisms were:

Staphylococcus aureus 2053 (methicillin-resistant)
Enterococcus faecalis 795 (vancomycin-susceptible)
Streptococcus pyogenes 717
Streptococcus pneumoniae 880 (penicillin-resistant)
Escherichia coli 102 (ATCC 25922)

The control organism tested with the control combinations of agents was Staphylococcus aureus 100 (ATCC 29213).

Streptococci were tested in Mueller Hinton II Broth (Becton Dickinson; Lot 7024879 and 7143673) supplemented with 2% lysed horse blood (Cleveland Scientific, Bath, Ohio; Lot 1110472). All other organisms were tested in Mueller Hinton II Broth. The broth was prepared at 1.05× normal weight/volume to offset the 5% volume of the drugs in the final test plates.

FIC values were determined using a broth microdilution method previously described. See, Sweeney, M T and Zurenko, G E. 2003. In vitro activities of linezolid combined with other antimicrobial agents against staphylococci, enterococci, pneumococci and selected Gram-negative organisms. Antimicrob. Agents Chemother. 47:1902-1906. Automated liquid handlers (Multidrop 384, Labsystems, Helsinki, Finland; Biomek 2000 and Multimek 96, Beckman Coulter, Fullerton Calif.) were used to conduct serial dilutions and liquid transfers.

The wells (columns 2-12) of standard 96-well microdilution plates (Falcon 3918) were filled with 150 μL of 50% DMSO using the Multidrop 384. Column 1 wells were filled with 300 μl of the 40× stock solutions. These plates were used to prepare the drug "mother plates" which provided the serial drug dilutions for the drug combination plates. The Biomek 2000 was used to prepare serial two-fold dilutions of the mother plate. Two mother plates, one for each drug, were combined to form a "checkerboard" pattern by transfer of equal volumes (using a multi-channel pipette) to the drug combination plate. Row H and Column 8 each contained serial dilutions of one of the test agents alone for determination of the MIC.

The "daughter plates" were loaded with 180 μL of test medium using the Multidrop 384. Then, the Multimek 96 was used to transfer 10 μL of drug solution from each well of the drug combination mother plate to each corresponding well of the daughter plate in a single step. Finally, the daughter plates were inoculated with test organism. Standardized inoculum of each organism was prepared per published guidelines. See, Clinical and Laboratory Standards Institute. *Methods for Dilution Antimicrobial Susceptibility Tests for Bacteria That Grow Aerobically; Approved Standard—Seventh Edition*. Clinical and Laboratory Standards Institute document M7-A7 [ISBN 1-56238-587-9]. Clinical and Laboratory Standards Institute, 940 West Valley Road, Suite 1400, Wayne, Pa. 19087-1898 USA, 2006.

The inoculum for each organism was dispensed into sterile reservoirs divided by length (Beckman Coulter), and the Biomek 2000 was used to inoculate the plates. The instrument delivered 10 μL of standardized inoculum into each well to yield a final cell concentration in the daughter plates of approximately $5 \times 10^5$ colony-forming-units/mL.

The test format resulted in the creation of an 8×8 checkerboard where each compound was tested alone (Column 8 and Row H) and in combination at varying ratios of drug concentration. Assay reproducibility was monitored using S. aureus 0100 (ATCC 29213) and the combination of amoxicillin-clavulanate, which yields a synergistic result with this test strain due to its β-lactamase-positive status. Chloramphenicol and sparfloxacin were used as a combination that may be antagonistic to demonstrate a negative interaction of a drug combination.

Test plates were stacked 3 high, covered with a lid on the top plate, placed in plastic bags, and incubated at 35° C. for approximately 20 hours. Following incubation, the microplates were removed from the incubator and viewed from the bottom using a ScienceWare plate viewer. Prepared reading sheets were marked for the MIC of drug 1 (row H), the MIC of drug 2 (column 8) and the wells of the growth-no growth interface.

An Excel program was used to determine the FIC according to the formula: (MIC of Compound 1 in combination/MIC of Compound 1 alone)+(MIC of Compound 2 in combination/MIC of Compound 2 alone). The FICI for the checkerboard was calculated from the individual FICs by the formula: $(FIC_1 + FIC_2 + \ldots FIC_n)/n$, where n=number of individual wells per plate for which FICs were calculated. In instances where an agent alone yielded an off-scale MIC result, the highest concentration was used as the MIC value in the FIC calculation.

All of the agents (and combinations of agents) were soluble at all final test concentrations (data not shown). Two control drug combinations were included in each FIC assay (Table 4). The combination amoxicillin-clavulanic acid demonstrated the expected synergistic interaction (FICI of $\leq 0.50$) for the control organism S. aureus 0100 in all FIC assays. The combination chloramphenicol-sparfloxacin, expected to demonstrate a negative interaction, yielded high FICI values that was categorized as antagonism in 7 of 8 determinations and no interaction in the remaining assay.

The MIC and FICI values are detailed in Tables 5 to 8. The interpretation listed in the tables for each test organism and drug combination is based upon the recently published FICI criteria. See, Odds F C. 2003. Synergy, antagonism, and what the chequerboard puts between them. J. Antimicrob. Chemother. 52(1):1. TR-700 demonstrated no interaction when assessed in combination with daptomycin against the Gram-positive test strains of S. aureus 2053 (Table 5), E. faecalis 795 (Table 6), S. pyogenes 717 (Table 7), and S. pneumoniae (Table 8).

One finding of this study is that the combination of TR-700 with daptomycin does not result in antagonistic interactions. Therefore, the combination of TR-700 with daptomycin could be employed in clinical circumstances where the use of combination therapy is indicated.

TABLE 4

Summary of Fractional Inhibitory Concentration Index (FICI) Values for Staphylococcus aureus 100 (ATCC 29213) and Control Combinations

| Compound 1 | | Compound 2 | | | | |
|---|---|---|---|---|---|---|
| Name | MIC (μg/ml) | Name | MIC (μg/ml) | FICI | Interpretation | Date |
| Amoxicillin | 2 | Clavulanate | 16 | 0.17 | Synergy | 20 Mar. 2008 |
|  | 1 |  | 16 | 0.29 | Synergy | 26 Mar. 2008 |

TABLE 4-continued

Summary of Fractional Inhibitory Concentration Index (FICI) Values for
*Staphylococcus aureus* 100 (ATCC 29213) and Control Combinations

| Compound 1 | | Compound 2 | | | | |
|---|---|---|---|---|---|---|
| Name | MIC (µg/ml) | Name | MIC (µg/ml) | FICI | Interpretation | Date |
| | 0.5 | | 16 | 0.41 | Synergy | 02 Apr. 2008 |
| | 2 | | 16 | 0.14 | Synergy | 09 Apr. 2008 |
| | 4 | | 16 | 0.10 | Synergy | 17 Apr. 2008 |
| | 2 | | 16 | 0.35 | Synergy | 30 Apr. 2008 |
| | 2 | | 16 | 0.35 | Synergy | 09 May 2008 |
| | 1 | | 16 | 0.41 | Synergy | 21 May 2008 |
| Chloramphenicol | 8 | Sparfloxacin | 0.03 | 5.51 | Antagonism | 20 Mar. 2008 |
| | 4 | | 0.03 | 6.17 | Antagonism | 26 Mar. 2008 |
| | 2 | | 0.015 | 6.51 | Antagonism | 02 Apr. 2008 |
| | 8 | | 0.06 | 3.16 | No Interaction | 09 Apr. 2008 |
| | 4 | | 0.03 | 7.42 | Antagonism | 17 Apr. 2008 |
| | 16 | | 0.06 | 4.08 | Antagonism | 30 Apr. 2008 |
| | 8 | | 0.008 | 6.33 | Antagonism | 09 May 2008 |
| | 4 | | 0.008 | 4.34 | Antagonism | 21 May 2008 |

TABLE 5

Summary of Fractional Inhibitory Concentration Index (FICI)
Values for *Staphylococcus aureus* 2053 (MRSA)

| | Compound | TR-700 | | |
|---|---|---|---|---|
| Name | MIC (µg/mL) | MIC (µg/mL) | FICI | Interpretation |
| Daptomycin | 0.5 | 0.5 | 1.16 | No Interaction |

TABLE 6

Summary of Fractional Inhibitory Concentration Index (FICI)
Values for *Enterococcus faecalis* 795 (VSE)

| | Compound | TR-700 | | |
|---|---|---|---|---|
| Name | MIC (µg/mL) | MIC (µg/mL) | FICI | Interpretation |
| Daptomycin | 1 | 0.5 | 0.70 | No Interaction |

TABLE 7

Summary of Fractional Inhibitory Concentration Index (FICI)
Values for *Streptococcus pyogenes* 717

| | Compound | TR-700 | | |
|---|---|---|---|---|
| Name | MIC (µg/mL) | MIC (µg/mL) | FICI | Interpretation |
| Daptomycin | 0.06 | 0.125 | 0.75 | No Interaction |

TABLE 8

Summary of Fractional Inhibitory Concentration Index (FICI)
Values for *Streptococcus pneumoniae* 880

| | Compound | TR-700 | | |
|---|---|---|---|---|
| Name | MIC (µg/mL) | MIC (µg/mL) | FICI | Interpretation |
| Daptomycin | 0.125 | 0.25 | 0.86 | No Interaction |

What is claimed is:

1. A therapeutic combination comprising
   (i) an antibacterially effective amount of daptomycin; and
   (ii) a compound of formula

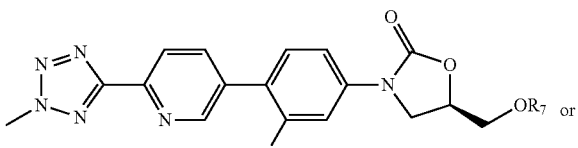

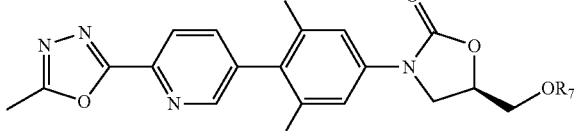

wherein $R_7$ is H, $PO(OH)_2$ or $PO(O)_2^{-2}(M^+)_2$, and wherein $M^+$ is $Na^+$, wherein the dosage of the compound of part (ii) is no more than about 1 mg/kg of body weight and wherein the dosage is effective to prevent the development of daptomycin non-susceptible bacterial strains.

2. The therapeutic combination of claim 1, wherein the compound of Formula (I) is

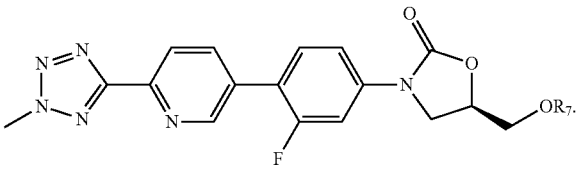

3. The therapeutic combination of claim 1,
   wherein the combination of the daptomycin and the compound do not act synergistically to enhance antibacterial potency, wherein the FICI is >0.50.

4. The therapeutic combination of claim 1,
   wherein each component of the therapeutic combination is formulated for separate or sequential administration.

5. The therapeutic combination of claim 1,
wherein the therapeutic combination is formulated for simultaneous administration.

6. A method of treating a methicillin resistant *S. aureus* (MRSA) infection in a subject, comprising administering to the subject the therapeutic combination of claim 1.

7. A method of treating a methicillin resistant *S. aureus* (MRSA) infection in a subject, comprising administering to the subject the therapeutic combination of claim 2.

8. The method of claim 6, wherein the bacterially infected subject has a bacterial infection that requires treatment for greater than two weeks.

9. The method of claim 7, wherein the bacterially infected subject has a bacterial infection that requires treatment for greater than two weeks.

10. The method of claim 6, wherein the bacterial infection is a bacterial skin and skin structure infection or bacteremia.

11. The method of claim 6, wherein the subject has endocarditis.

12. The method of claim 9, wherein the administering step further comprises administering the therapeutic combination for at least two weeks.

13. The method of claim 7, wherein the administering step further comprises administering the same amount of daptomycin until the infection is resolved.

14. The therapeutic combination of claim 2,
wherein each component of the therapeutic combination is formulated for separate or sequential administration.

15. The therapeutic combination of claim 2,
wherein the therapeutic combination is formulated for simultaneous administration.

16. The therapeutic combination of claim 2, wherein the dosage of the compound of Formula (I) is no more than about 0.5 mg/kg.

17. The method of claim 7, wherein the bacterial infection is a bacterial skin and skin structure infection or bacteremia.

18. The method of claim 7, wherein the subject has endocarditis.

* * * * *